US011542245B2

(12) United States Patent
Egger et al.

(10) Patent No.: US 11,542,245 B2
(45) Date of Patent: Jan. 3, 2023

(54) PREPARATIVE PROCESS

(71) Applicants: Bayer Aktiengesellschaft, Leverkusen (DE); Bayer Pharma Aktiengesellschaft, Berlin (DE)

(72) Inventors: Julian Egger, Remscheid (DE); Daniel Goetz, Duesseldorf (DE); Michal Sowa, Wuppertal (DE)

(73) Assignee: BAYER PHARMA AKTIENGESELLSCHAFT, Leverkusen (DE)

( * ) Notice: Subject to any disclaimer, the term of this patent is extended or adjusted under 35 U.S.C. 154(b) by 70 days.

(21) Appl. No.: 16/980,210

(22) PCT Filed: Mar. 8, 2019

(86) PCT No.: PCT/EP2019/055815
§ 371 (c)(1),
(2) Date: Sep. 11, 2020

(87) PCT Pub. No.: WO2019/175043
PCT Pub. Date: Sep. 19, 2019

(65) Prior Publication Data
US 2021/0017152 A1    Jan. 21, 2021

(30) Foreign Application Priority Data
Mar. 15, 2018   (EP) .................... 18161983

(51) Int. Cl.
*C07D 401/10*    (2006.01)
(52) U.S. Cl.
CPC ................. *C07D 401/10* (2013.01)
(58) Field of Classification Search
CPC .................................. C07D 401/10
See application file for complete search history.

(56) References Cited

U.S. PATENT DOCUMENTS

| 9,434,690 | B2 | 9/2016 | Roehrig et al. |
| 9,822,102 | B2 | 11/2017 | Roehrig et al. |
| 10,183,932 | B2 | 1/2019 | Roehrig et al. |
| 10,421,742 | B2 | 9/2019 | Jimenez Nunez et al. |
| 2016/0052884 | A1* | 2/2016 | Rohrig ...................... A61P 7/00 546/261 |
| 2019/0367478 | A1 | 12/2019 | Jimenez Nunez et al. |

FOREIGN PATENT DOCUMENTS

| WO | 2014/154794 A1 | 10/2014 | |
| WO | 2017/005725 A1 | 1/2017 | |
| WO | WO-2020126682 A1 * | 6/2020 | ......... A61K 31/4439 |
| WO | WO-2020127504 A1 * | 6/2020 | ......... C07D 491/044 |
| WO | WO-2020127508 A1 * | 6/2020 | ......... C07D 491/044 |

OTHER PUBLICATIONS

PCT International Search Report for PCT/EP2019/055815, dated Jun. 18, 2019.
Dragovich, et al., "Structure-Based Design, Synthesis, and Biological Evaluation of Irreversible Human Rhinovirus 3C Protease Inhibitors. 8. Pharmacological Optimization of Orally Bioavailable 2-Pyridone-Containing Peptidomimetics," J. Med. Chem., (2003), vol. 46: 4572-4585.
Chen, et al., "A Simple Preparation of a (Pyridonyl-1)propargylacetic Acid Derivative," Organic Process Research & Development, (2006), vol. 10: 838-840.
Guram, et al., "New Air-Stable Catalysts for General and Efficient Suzuki-Miyaura Cross-Coupling Reactions of Heteroaryl Chlorides," Organic Letters, (2006), vol. 8, No. 9: 1787-1789.
Compagnone, et al., "Chirospecific Synthesis of ( + )-Pilocarpine," J. Org. Chem., (1986), vol. 51: 1713-1719.
Dunetz, et al., "General and Scalable Amide Bond Formation with Epimerization-Prone Substrates Using T3P and Pyridine," Organic Letters, (2011), vol. 13, No. 19: 5048-5051.

* cited by examiner

*Primary Examiner* — Daniel R Carcanague
(74) *Attorney, Agent, or Firm* — McBee Moore & Vanik IP, LLC

(57) ABSTRACT

The present invention relates to a process for preparing 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I) or 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) from 2,5-dimethoxypyridine (III), 1-(2-bromo-4-chlorophenyl)-4-chloro-1H-1,2,3-triazole (X-Cl) or 1-(2-bromo-4-chlorophenyl)-4-(trifluoromethyl)-1H-1,2,3-triazole (X-CF$_3$), 4-amino-2-fluorbenzamide (XIII) and (2R)-2-aminobutanoic acid (XVII).

17 Claims, 8 Drawing Sheets

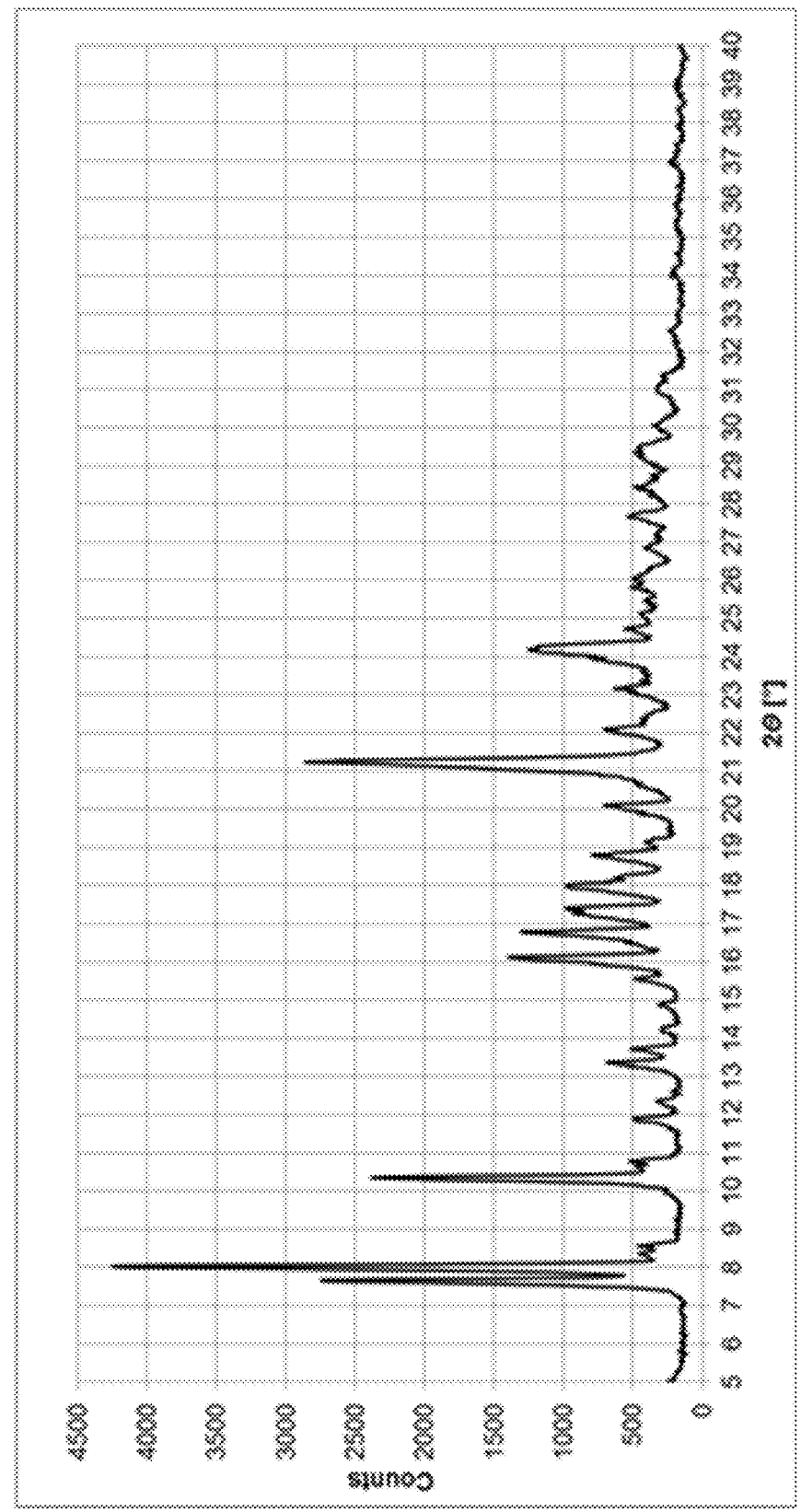
Figure 1. XRPD plot of the compound of the formula (IIa).

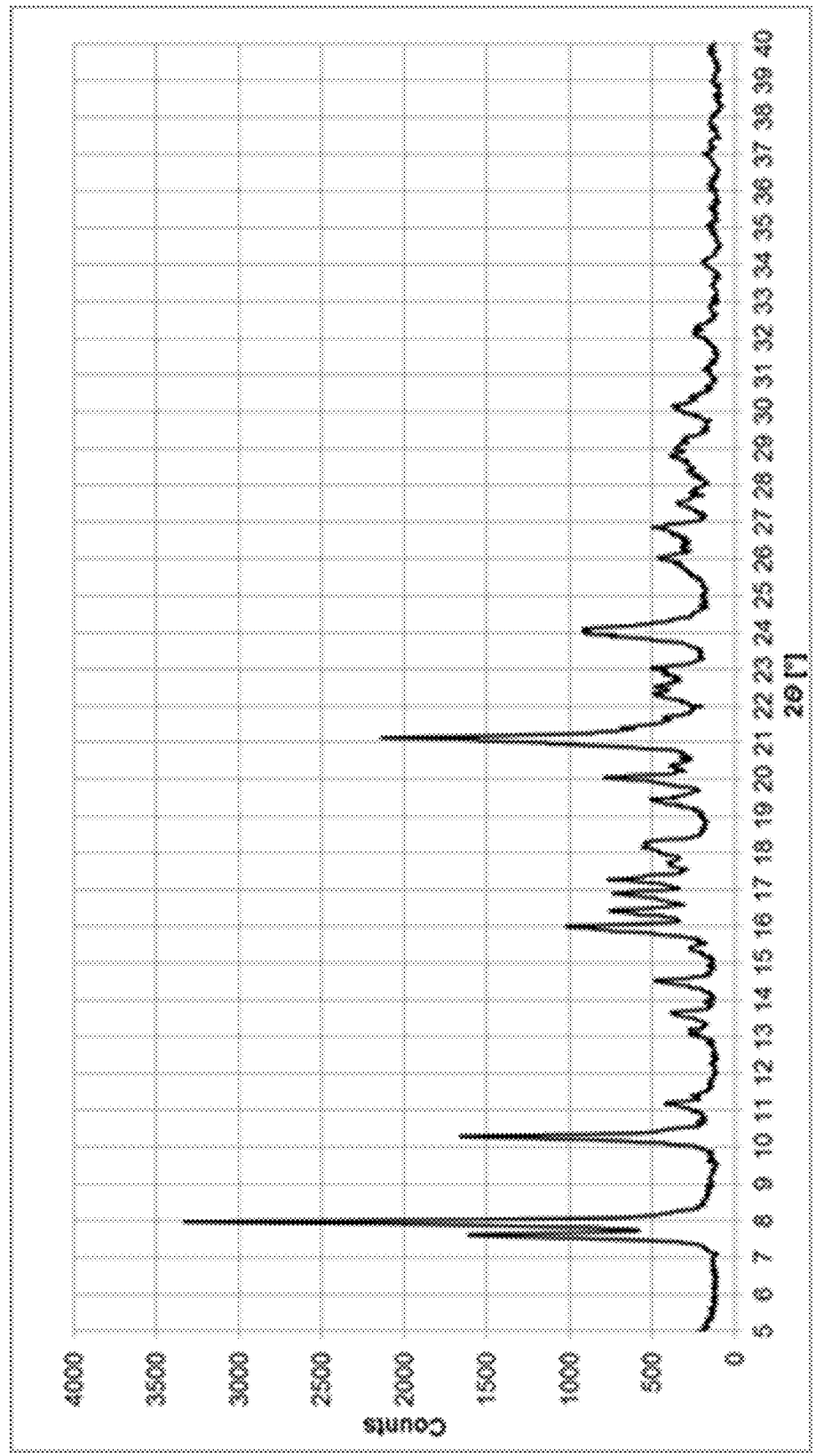
Figure 2. XRPD plot of the compound of the formula (IIb).

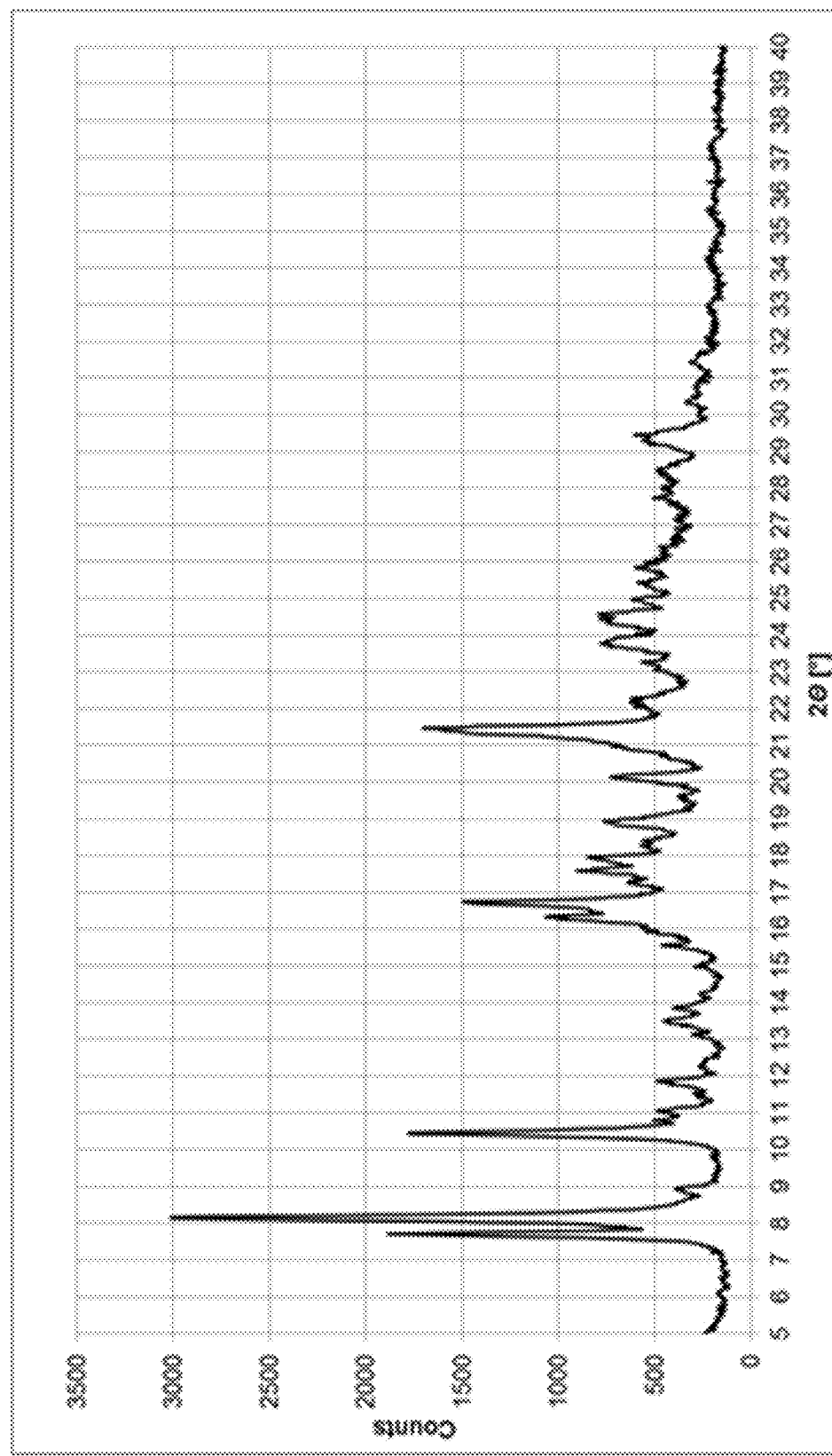
Figure 3. XRPD plot of the compound of the formula (IIc).

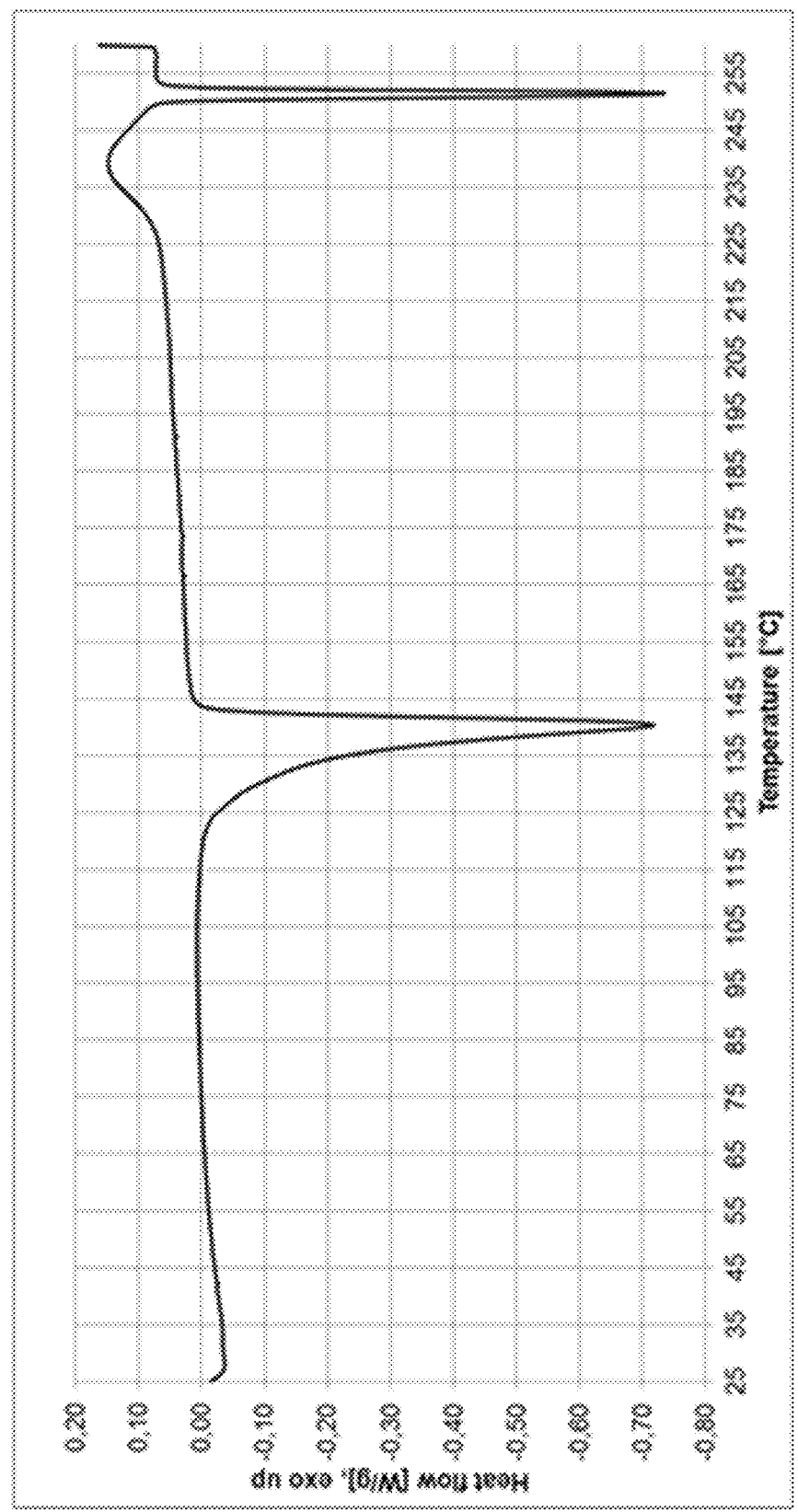
Figure 4. DSC plot of the compound of the formula (IIa).

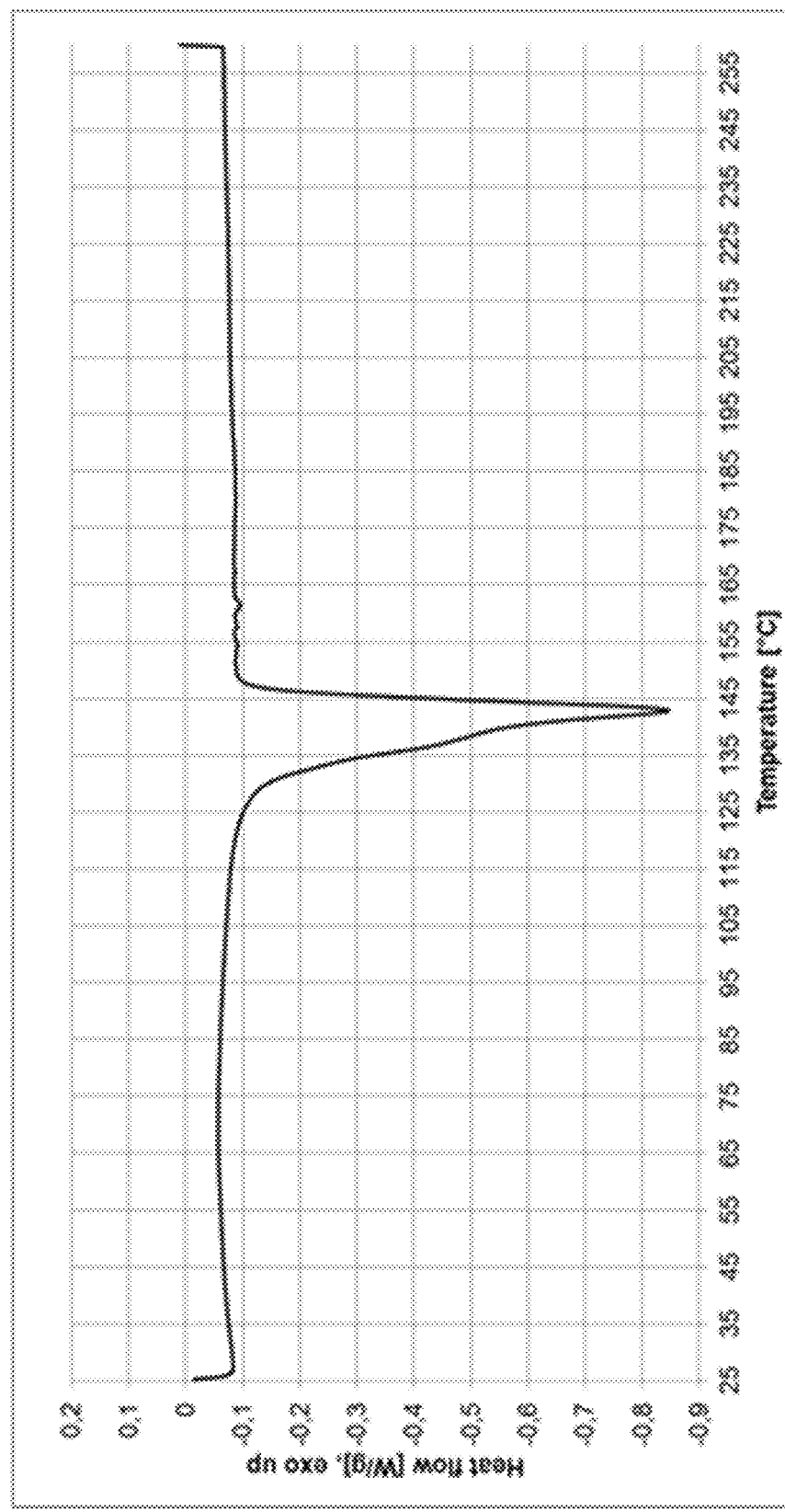
Figure 5. DSC plot of the compound of the formula (IIb).

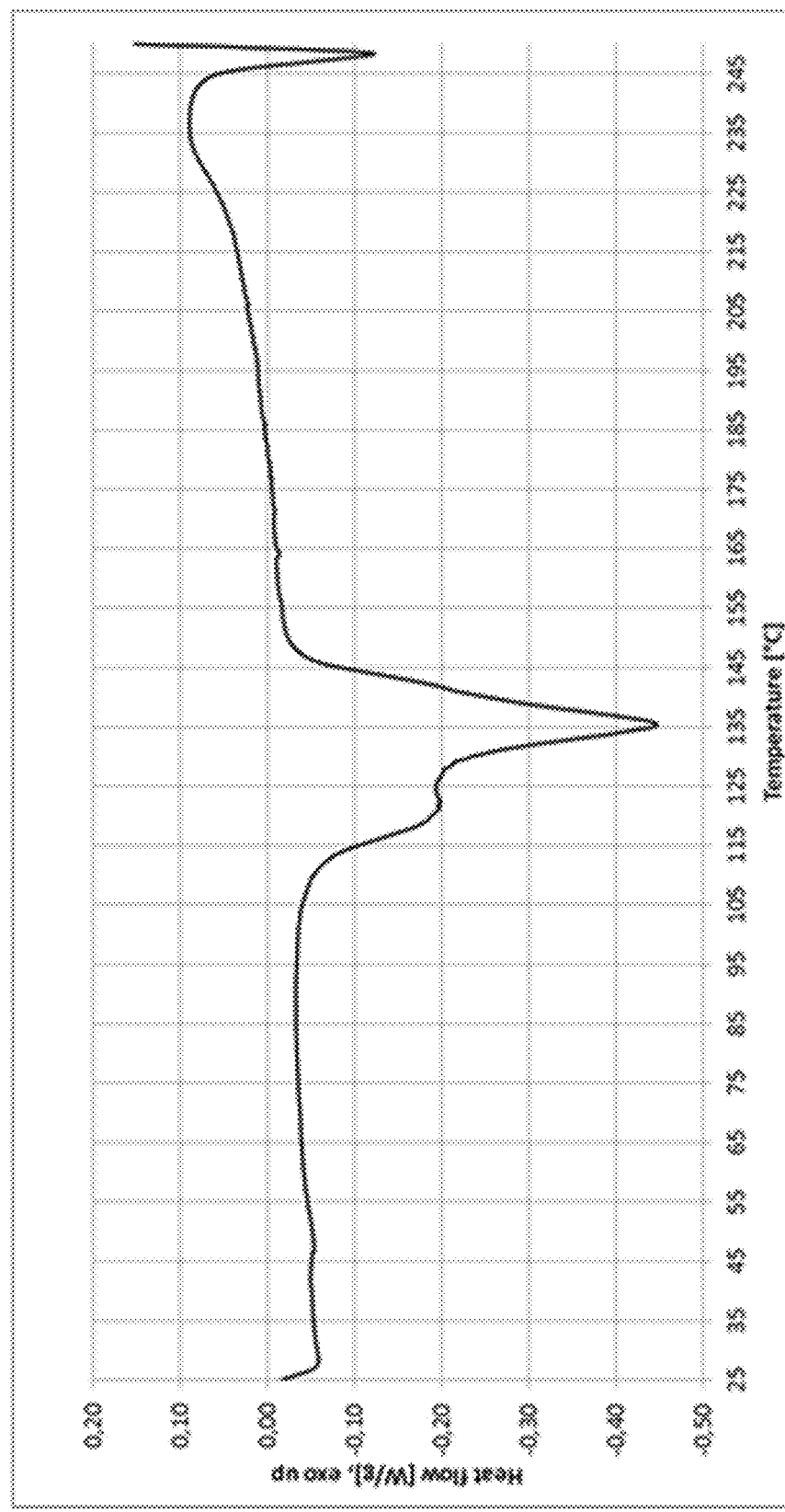
Figure 6. DSC plot of the compound of the formula (IIc).

Figure 7. Micrograph of the compound of the formula (IIa).
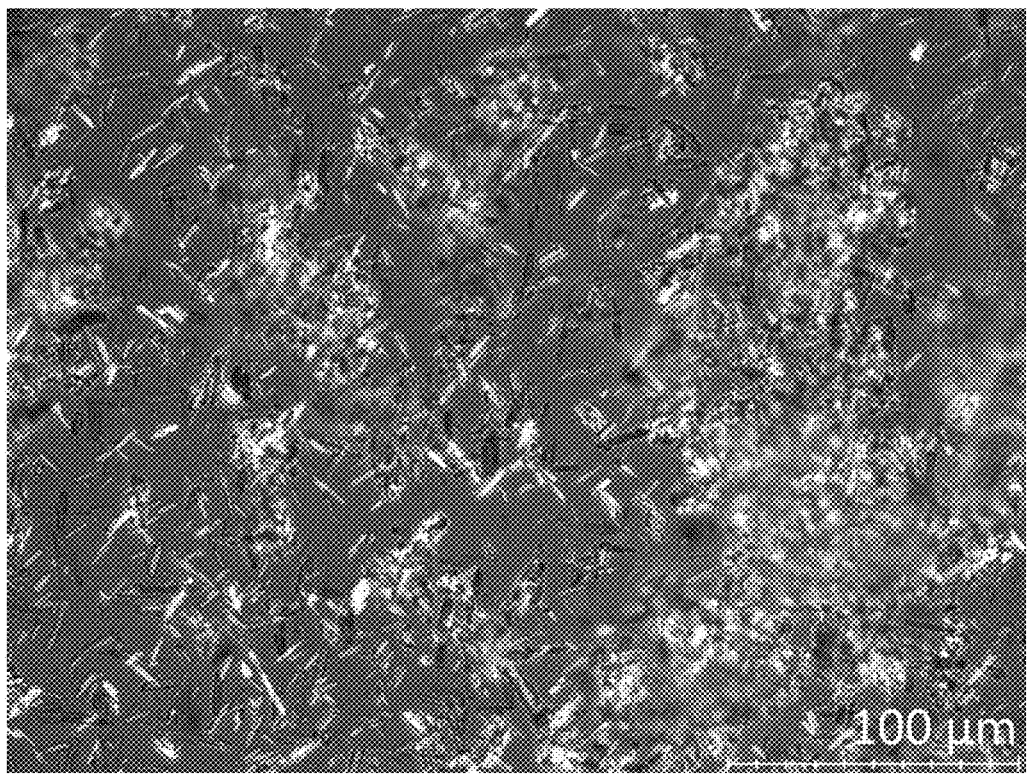
Figure 8. Micrograph of the compound of the formula (IIb).
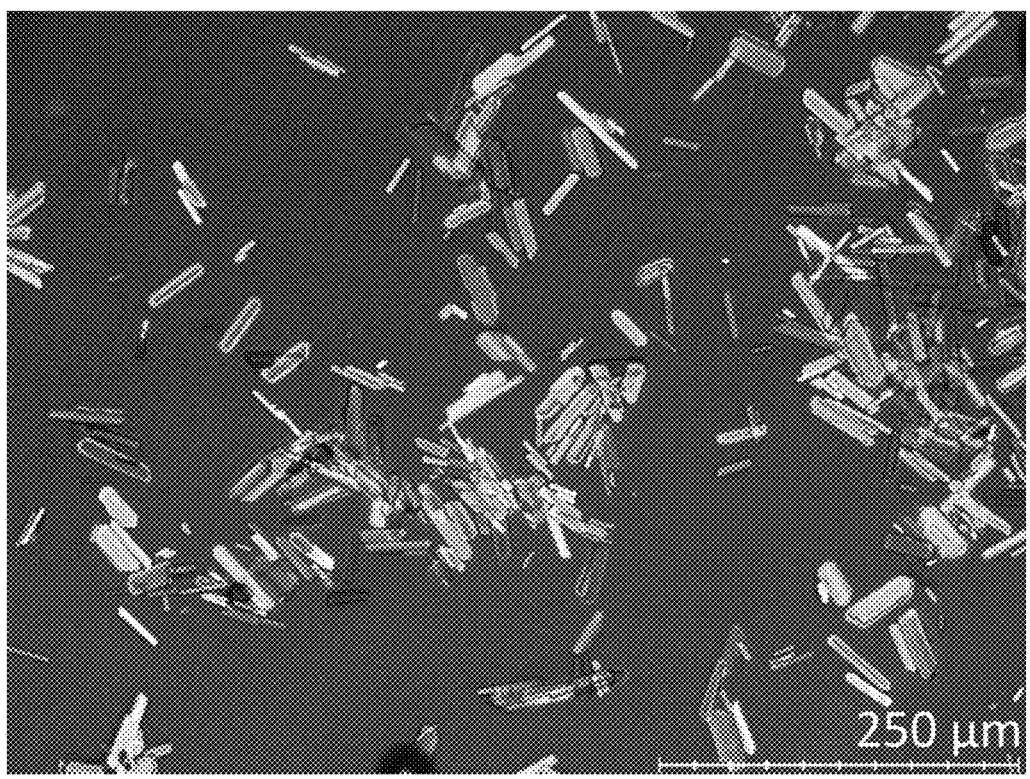

Figure 9. Micrograph of the compound of the formula (IIc).
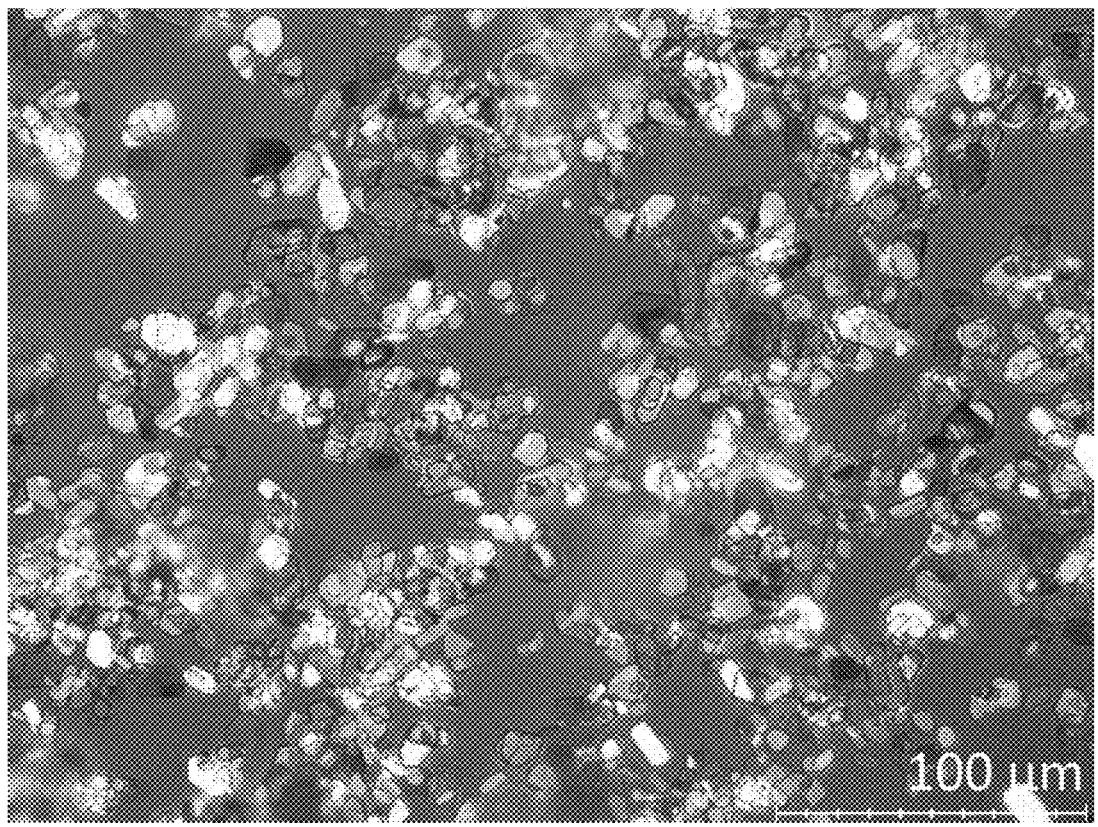

PREPARATIVE PROCESS

CROSS-REFERENCE TO RELATED APPLICATIONS

This application is the National Stage entry of International Application No. PCT/EP2019/055815, filed 8 Mar. 2019, which claims priority to European Patent Application No. 18161983.4, filed 15 Mar. 2018.

BACKGROUND

Field

The present invention relates to a process for preparing 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I) or 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) from 2,5-dimethoxypyridine (III), 1-(2-bromo-4-chlorophenyl)-4-chloro-1H-1,2,3-triazole (X-Cl) or 1-(2-bromo-4-chlorophenyl)-4-(trifluoromethyl)-1H-1,2,3-triazole (X-CF$_3$), 4-amino-2-fluorbenzamide (XIII) and (2R)-2-aminobutanoic acid (XVII).

Description of Related Art

The compounds 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I) and 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide (II) are known from WO 2017/005725 and correspond to the formulae (I) and (II)

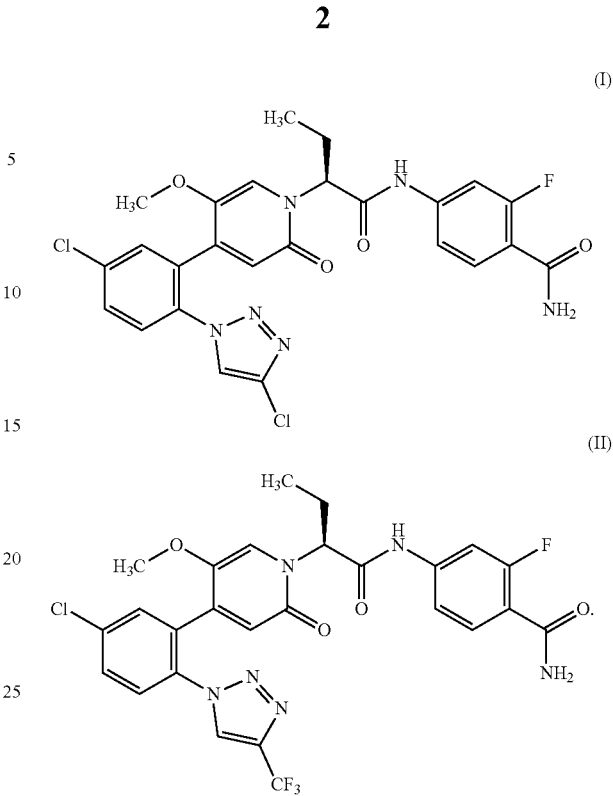

The compounds of the formulae (I) and (II) act as inhibitors for the Factor XIa and owing to this specific mechanism of action, might lead in vivo after oral administration to a safe and efficient anticoagulation.

WO 2014/154794 and WO 2017/005725 describe a synthesis for preparing the compounds of the formulae (I) and (II) in the gram range starting from 2,5-dimethoxypyridine (III), 1-(2-bromo-4-chlorophenyl)-4-chloro-1H-1,2,3-triazole (X-Cl) or 1-(2-bromo-4-chlorophenyl)-4-(trifluoromethyl)-1H-1,2,3-triazole (X-CF$_3$) respectively, 4-amino-2-fluorobenzamide (XIII) and tert-butyl 2-bromobutanoate (VII) (Scheme 1).

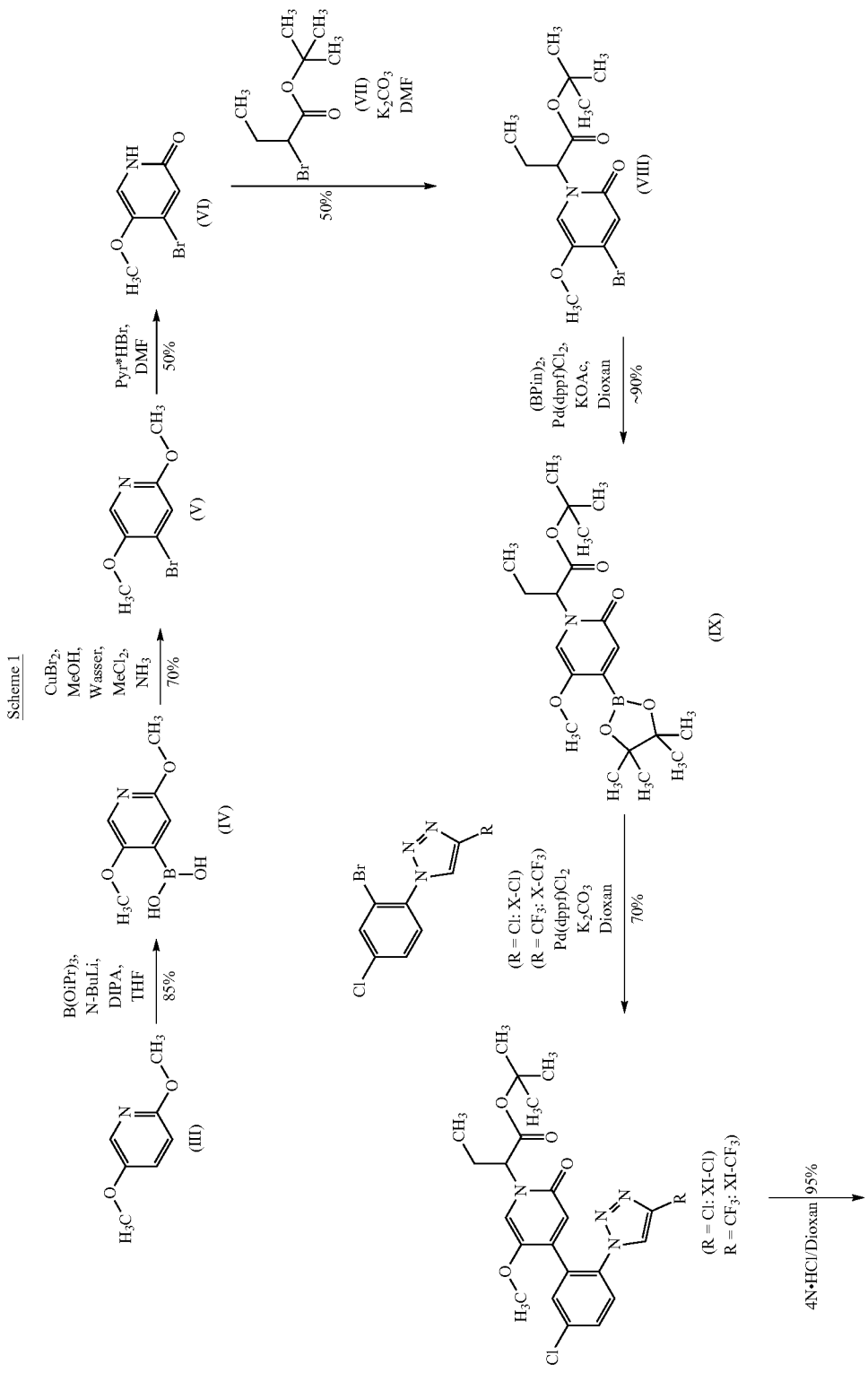

-continued
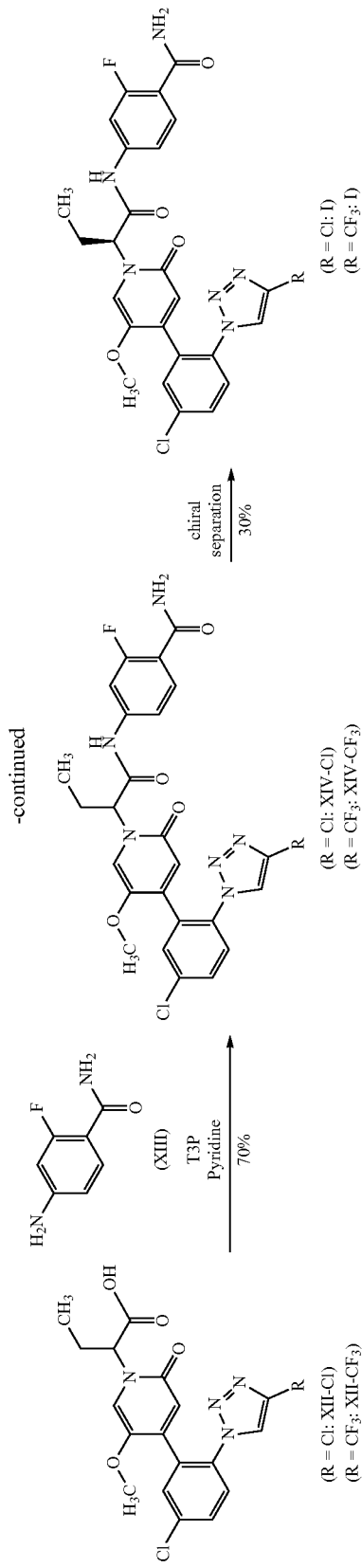

IUPAC Chemical names of the compounds (I) to (XIV-Cl)/(XIV-CF$_3$):

4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I), 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II), 2,5-dimethoxypyridine (III), (2,5-dimethoxypyridin-4-yl)boronic acid (IV), 4-bromo-2,5-dimethoxypyridine (V), 4-bromo-5-methoxypyridin-2(1H)-one (VI), tert-butyl 2-bromobutanoate (VII), tert-butyl 2-(4-bromo-5-methoxy-2-oxopyridin-1(2H)-yl)butanoate (VIII), tert-butyl 2-[5-methoxy-2-oxo-4-(4,4,5,5-tetramethyl-1,3,2-dioxaborolan-2-yl)pyridin-1(2H)-yl]butanoate (IX), 1-(2-bromo-4-chlorophenyl)-4-chloro-1H-1,2,3-triazole (X-Cl), 1-(2-bromo-4-chlorophenyl)-4-(trifluoromethyl)-1H-1,2,3-triazole (X-CF$_3$), tert-butyl 2-{4-[5-chloro-2-(4-chloro-1H-1,2,3-triazol-1-yl)phenyl]-5-methoxy-2-oxopyridin-1(2H)-yl}butanoate (XI-Cl), tert-butyl 2-[4-{5-chloro-2-[4-(trifluoromethyl)-1H-1,2,3-triazol-1-yl]phenyl}-5-methoxy-2-oxopyridin-1(2H)-yl]butanoate (XI-CF$_3$), 2-{4-[5-chloro-2-(4-chloro-1H-1,2,3-triazol-1-yl)phenyl]-5-methoxy-2-oxopyridin-1(2H)-yl}butanoic acid (XII-Cl), 2-[4-{5-chloro-2-[4-(trifluoromethyl)-1H-1,2,3-triazol-1-yl]phenyl}-5-methoxy-2-oxopyridin-1(2H)-yl]butanoic acid (XII-CF$_3$), 4-amino-2-fluorobenzamide (XIII), 4-(2-{4-[5-chloro-2-(4-chloro-1H-1,2,3-triazol-1-yl)phenyl]-5-methoxy-2-oxopyridin-1(2H)-yl}butanamido)-2-fluorobenzamide (XIV-Cl), 4-{2-[4-{5-chloro-2-[4-(trifluoromethyl)-4,5-dihydro-1H-1,2,3-triazol-1-yl]phenyl}-5-methoxy-2-oxopyridin-1(2H)-yl]butanamido}-2-fluorobenzamide (XIV-CF$_3$).

The synthesis of the compounds of the formulae (I) and (II), mentioned in scheme 1, can be divided into three sections:

a) Preparation of tert-butyl 2-{4-[5-chloro-1H-1,2,3-triazol-1-yl)phenyl]-5-methoxy-2-oxopyridin-1(2H)-yl}butanoate (XI-Cl) or tert-butyl 2-[4-{5-chloro-2-[4-(trifluoromethyl)-1H-1,2,3-triazol-1-yl]phenyl}-5-methoxy-2-oxopyridin-1(2H)-yl]butanoate (XI-CF$_3$) from 2,5-dimethoxypyridine (III) and 1-(2-bromo-4-chlorophenyl)-4-chloro-1H-1,2,3-triazole (X-Cl) or 1-(2-bromo-4-chlorophenyl)-4-(trifluoromethyl)-1H-1,2,3-triazole (X-CF$_3$) respectively via tert-butyl 2-[5-methoxy-2-oxo-4-(4,4,5,5-tetramethyl-1,3,2-dioxaborolan-2-yl)pyridin-1(2H)-yl]butanoate (IX).

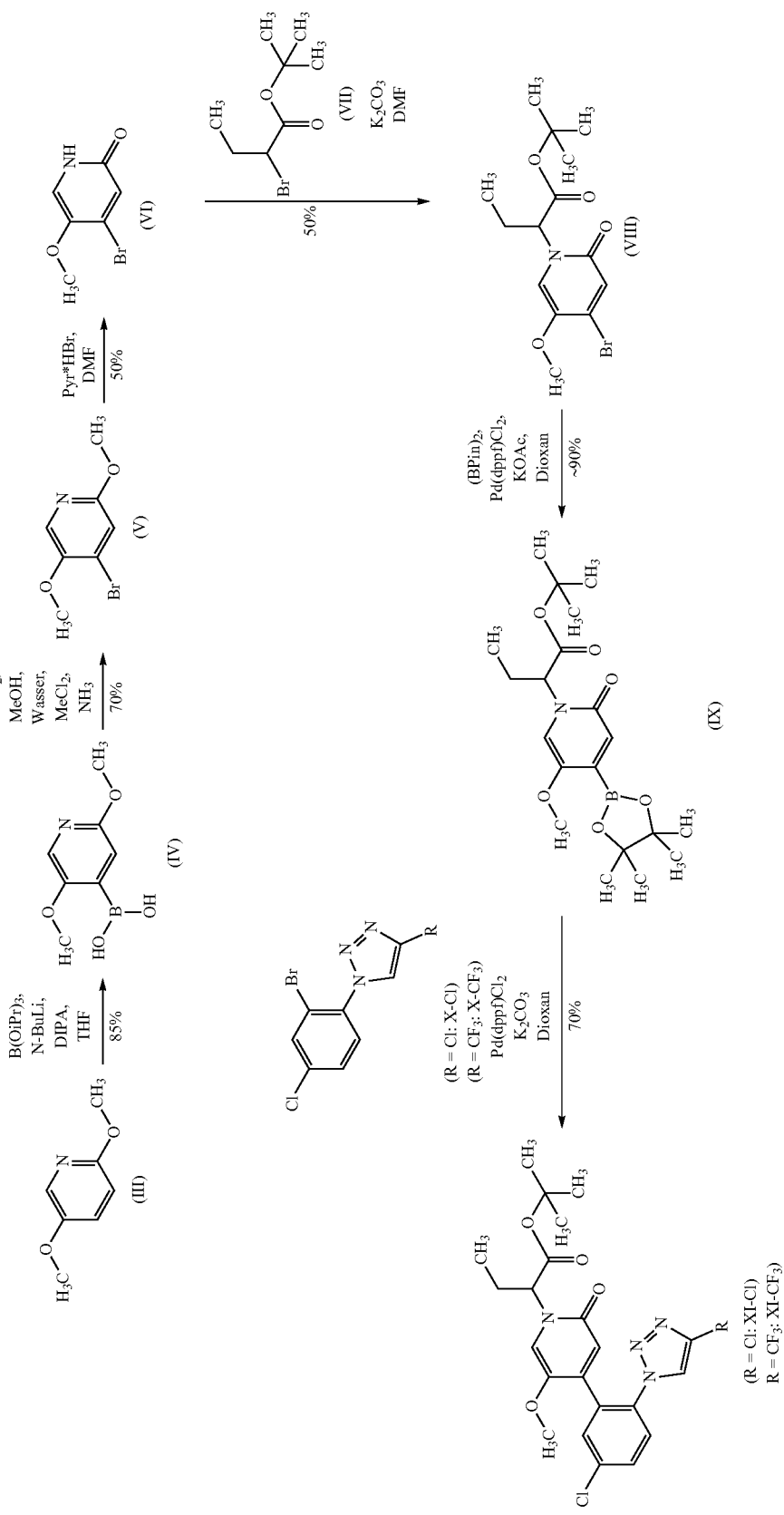

b) Preparation of 4-(2-{4-[5-chloro-2-(4-chloro-1H-1,2,3-triazol-1-yl)phenyl]-5-methoxy-2-oxopyridin-1(2H)-yl}butanamido)-2-fluorobenzamide (XIV-Cl) or 4-{2-[4-{5-chloro-2-[4-(trifluoromethyl)-4,5-dihydro-1H-1,2,3-triazol-1-yl]phenyl}-5-methoxy-2-oxopyridin-1(2H)-yl]butanamido}-2-fluorobenzamide (XIV-CF₃) from tert-butyl 2-{4-[5-chloro-2-(4-chloro-1H-1,2,3-triazol-1-yl)phenyl]-5-methoxy-2-oxopyridin-1(2H)-yl}butanoate (XI-Cl) or tert-butyl 2-[4-{5-chloro-2-[4-(trifluoromethyl)-1H-1,2,3-triazol-1-yl]phenyl}-5-methoxy-2-oxopyridin-1(2H)-yl]butanoate (XI-CF₃) respectively via 2-{4-[5-chloro-2-(4-chloro-1H-1,2,3-triazol-1-yl)phenyl]-5-methoxy-2-oxopyridin-1(2H)-yl}butanoic acid (XII-Cl) or 2-[4-{5-chloro-2-[4-(trifluoromethyl)-1H-1,2,3-triazol-1-yl]phenyl}-5-methoxy-2-oxopyridin-1(2H)-yl]butanoic acid (XII-CF₃) respectively and 4-amino-2-fluorobenzamide (XIII).

Scheme 3

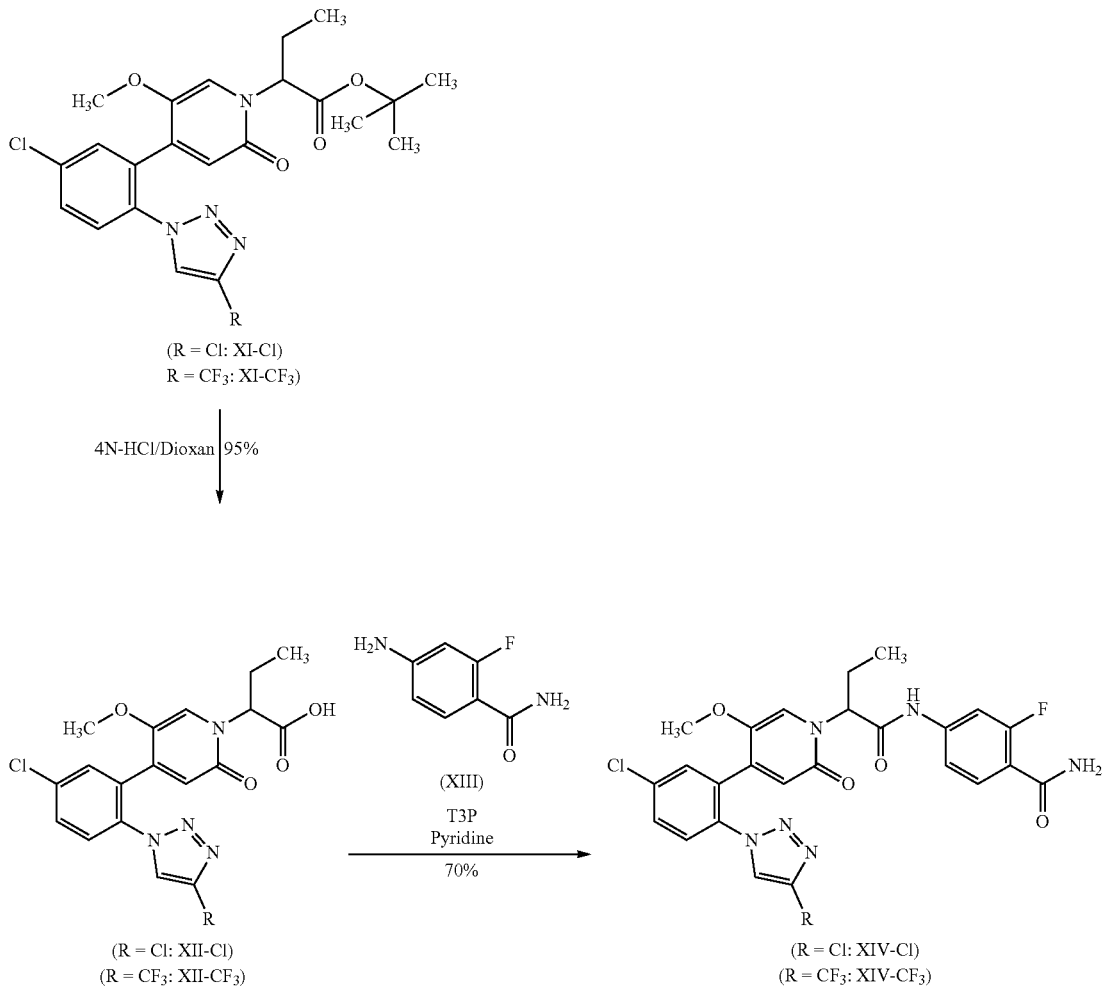

c) Separation of the two enantiomers of 4-(2-{4-[5-chloro-2-(4-chloro-1H-1,2,3-triazol-1-yl)phenyl]-5-methoxy-2-oxopyridin-1(2H)-yl}butanamido)-2-fluorobenzamide (XIV-Cl) or 4-{2-[4-{5-chloro-2-[4-(trifluoromethyl)-4,5-dihydro-1H-1,2,3-triazol-1-yl]phenyl}-5-methoxy-2-oxopyridin-1(2H)-yl]butanamido}-2-fluorobenzamide (XIV-CF₃) to obtain the single enantiomers 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I) or 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) respectively.

Scheme 4

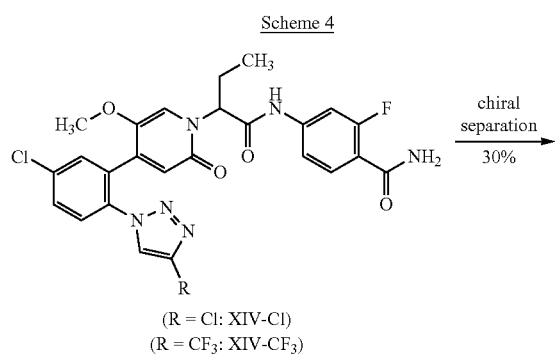

(R = Cl: XIV-Cl)
(R = CF$_3$: XIV-CF$_3$)

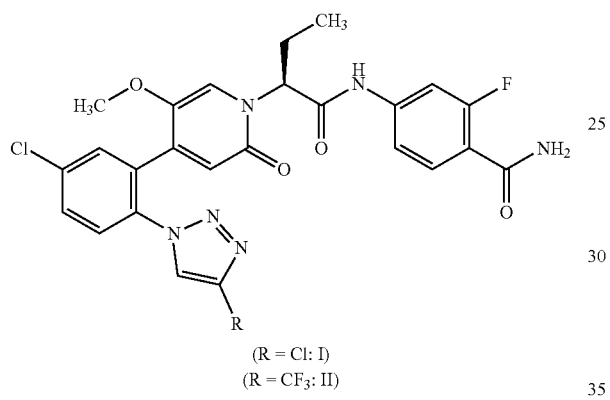

(R = Cl: I)
(R = CF$_3$: II)

For industrial implementation and the production of larger kilogram amounts, the preparative processes and route described in WO 2014/154794 and WO 2017/005725 are suitable to only a very limited extent. The route is lengthy (9 linear steps) and requires tedious work-up and purification procedures, resulting in a low overall yield. The biggest drawback is that the sequence provides material only in racemic form as compound of the formula (XIV-Cl)/(XIV-CF$_3$) and needs to be separated via a chiral chromatography to produce the desired single enantiomers of the compound of the formula (I)/(II). The sequence of the synthetic steps as described in WO 2014/154794 and WO 2017/005725, makes the development of an asymmetric version using the same intermediates hardly possible. Literature precedence indicates that the installation of a stereocenter between the pyridone ring and an ester, as in compounds of the formulae (VIII), (IX) and (XI-Cl)/(XI-CF$_3$), is a difficult task, due to the high tendency for racemization of this position in the molecule (P. S. Dragovich, et al., *J. Med. Chem.*, 2003, 46, 4572). Furthermore, there is clear evidence that under deprotection or amide coupling conditions such a stereocenter at a highly acidic position is very prone to racemization (L. Chen, et al., *Organic Process Research & Development*, 2006, 10, 838). The necessity of a chiral separation represents not only an economically unfavourable process, but also makes the production of the Active Pharmaceutical Ingredient (API) a time consuming endeavour.

SUMMARY

Thus a new synthetic route has surprisingly been found that copes with most of the challenges for the previous process described above in Scheme 1. The route described in Scheme 5 is much shorter with 4 steps in the longest linear sequence (6 in total). Higher yields for the individual steps are obtained which result in a higher overall yield for the entire sequence. The route is convergent which allows for pursuing synthetic steps in parallel and an optimized time management. Most importantly the new route follows an asymmetric strategy and provides the desired compound of the formula (I)/(II) in high enantiomeric excess (ee) without depending on an expensive and time consuming chiral separation via HPLC or SFC.

DETAILED DESCRIPTION OF A PREFERRED EMBODIMENT

Scheme 5

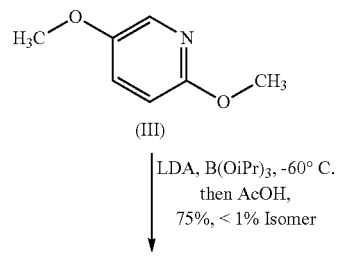

(III)

LDA, B(OiPr)$_3$, -60° C.
then AcOH,
75%, < 1% Isomer

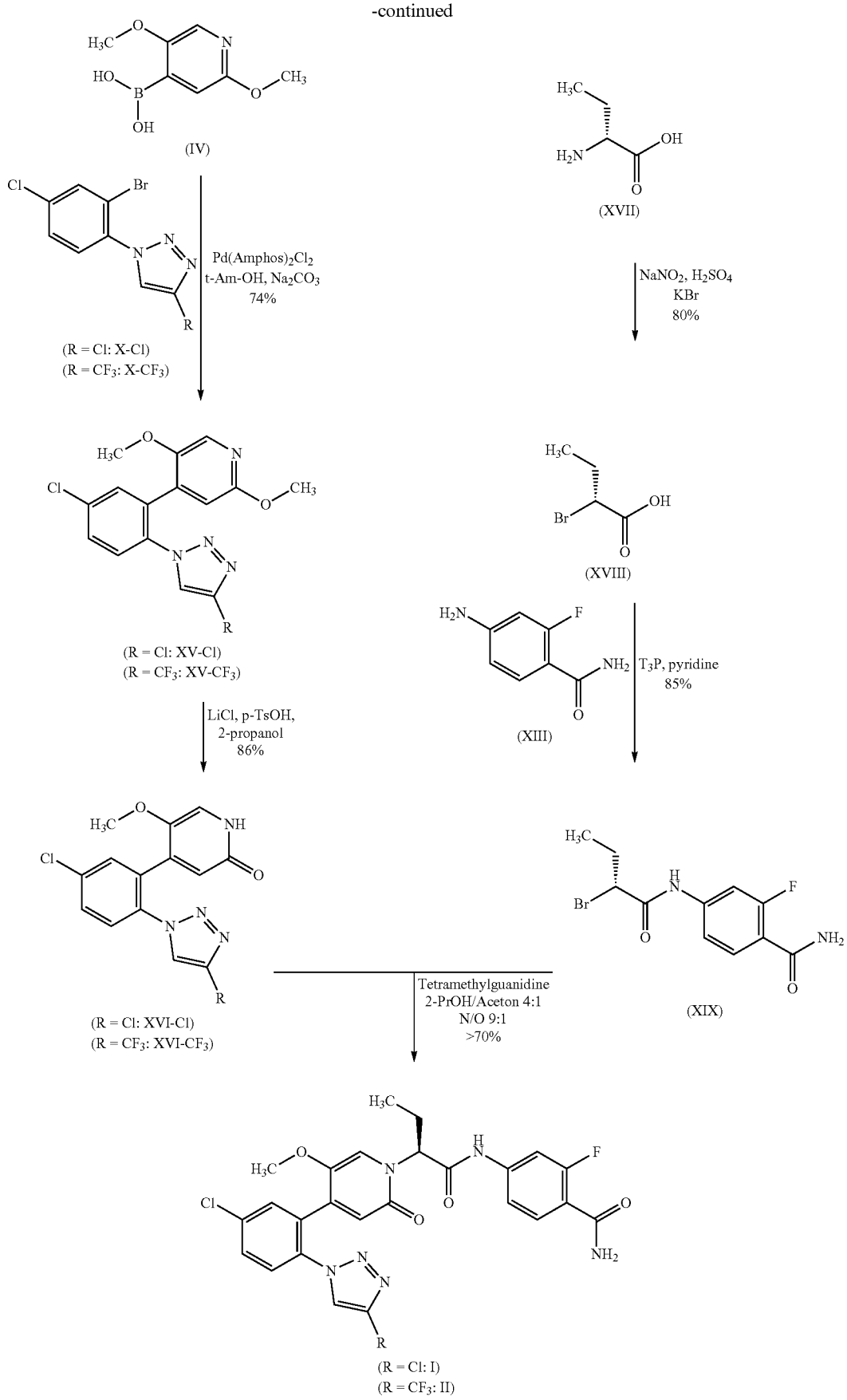
-continued

IUPAC Chemical names of the compounds (XV-Cl)/(XV-CF$_3$) to (XIX):

4-[5-chloro-2-(4-chloro-1H-1,2,3-triazol-1-yl)phenyl]-2,5-dimethoxy-pyridine (XV-Cl)

4-{5-chloro-2-[4-(trifluoromethyl)-1H-1,2,3-triazol-1-yl]phenyl}-2,5-dimethoxypyridine (XV-CF$_3$)

4-[5-chloro-2-(4-chloro-1H-1,2,3-triazol-1-yl)phenyl]-5-methoxypyridin-2(1H)-one (XVI-Cl)

4-{5-chloro-2-[4-(trifluoromethyl)-1H-1,2,3-triazol-1-yl]phenyl}-5-methoxypyridin-2(1H)-one (XVI-CF$_3$)

(2R)-2-aminobutanoic acid (XVII)

(2R)-2-bromobutanoic acid (XVIII)

4-{[(2R)-2-bromobutanoyl]amino}-2-fluorobenzamide (XIX)

The compound of the formula (II) can be converted into its respective solvates by treatment with the corresponding solvents. Solvates are in example isopropyl acetate, tetrahydrofuran and acetone resulting in the compound 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide isopropyl acetate (IIa), 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide tetrahydrofuran (IIb) and 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide acetone (IIc) respectively.

EXPLANATION OF THE FIGURES

FIG. 1: XRPD plot of the compound of the formula (IIa).
FIG. 2: XRPD plot of the compound of the formula (IIb).
FIG. 3: XRPD plot of the compound of the formula (IIc).
FIG. 4: DSC plot of the compound of the formula (IIa).
FIG. 5: DSC plot of the compound of the formula (IIb).
FIG. 6: DSC plot of the compound of the formula (IIc).
FIG. 7: Micrograph of the compound of the formula (IIa).
FIG. 8: Micrograph of the compound of the formula (IIb).
FIG. 9: Micrograph of the compound of the formula (IIc).

In the case of the synthesis intermediates and working examples of the invention described hereinafter, any compound specified in the form of a solvate is generally a solvate of unknown exact stoichiometric composition, as obtained by the respective preparation and/or purification process. Unless specified in more detail, additions to names and structural formulae, such as "isopropyl acetate", "tetrahydrofuran" or "acetone" should not therefore be understood in a stoichiometric sense in the case of such solvates, but have merely descriptive character with regard to the solvate-forming components present therein.

Preferred are solvates with a stoichiometric composition of compound to solvent 1:1.

Comparison of Synthetic Sequences:

a) Compound of the formula (III) to compound of the formula (XI-Cl)/(XI-CF$_3$) via compound of the formula (IX) (described in WO 2017/005725) versus compound of the formula (III) to compound of the formula (XVI-Cl)/(XVI-CF$_3$) (present invention)

Compound of the Formula (III) to Compound of the Formula (XI-Cl)/(XI-CF$_3$) Via Compound of the Formula (IX) (Described in WO 2017/005725)

The sequence described in WO 2017/005725 and in parts in WO 2014/154794 starts with a lithiation-borylation sequence of 2,5-dimethoxypyridine (III) to provide (2,5-dimethoxypyridin-4-yl)boronic acid (IV), and in the next step the boryl group on the pyridine ring is replaced by a bromide to obtain 4-bromo-2,5-dimethoxypyridine (V). 4-Bromo-2,5-dimethoxypyridine (V) is then demethylated to obtain 4-bromo-5-methoxypyridin-2(1H)-one (VI) which is N-alkylated with tert-butyl 2-bromobutanoate (VII) to obtain tert-butyl 2-(4-bromo-5-methoxy-2-oxopyridin-1(2H)-yl)butanoate (VIII). On the compound of the formula (VIII) a pinacol boronic ester is installed in a Pd-catalyzed borylation reaction to obtain tert-butyl 2-[5-methoxy-2-oxo-4-(4,4,5,5-tetramethyl-1,3,2-dioxaborolan-2-yl)pyridin-1(2H)-yl]butanoate (IX). The compound of the formula (IX) is then coupled with the 1-(2-bromo-4-chlorophenyl)-4-chloro-1H-1,2,3-triazole (X-Cl)/1-(2-bromo-4-chlorophenyl)-4-(trifluoromethyl)-1H-1,2,3-triazole (X-CF$_3$) to obtain the intermediate tert-butyl 2-{4-[5-chloro-2-(4-chloro-1H-1,2,3-triazol-1-yl)phenyl]-5-methoxy-2-oxopyridin-1(2H)-yl}butanoate (XI-Cl)/tert-butyl 2-[4-{5-chloro-2-[4-(trifluoromethyl)-1H-1,2,3-triazol-1-yl]phenyl}-5-methoxy-2-oxopyridin-1(2H)-yl]butanoate (XI-CF$_3$). Even though the sequence allows completion of the target compound of the formula (I)/(II), it comes with some drawbacks for the preparation of the molecules on larger scale. The installation of the bromide on the pyridine (compound of the formula (V)) via a boronic acid (compound of the formula (IV)) is a relatively uneconomic and low yielding procedure, especially since another boronic ester is installed on the same position later in the sequence for the preparation of the compound of the formula (IX). In addition, use of the reagent (Bis)pinacolatodiboron in the step from compound of the formula (VIII) to compound of the formula (IX) and the catalyst Pd(dppf)Cl$_2$ in the transformations from compound of the formula (VIII) to compound of the formula (IX) and compound of the formula (IX) to compound of the formula (XI-Cl)/(XI-CF$_3$) make the sequence relatively cost-intensive. Furthermore, the sequence requires the non-advantageous solvents DMF and dioxane in the transformations from the compound of the formula (V) to the compound of the formula (XI-Cl)/(XI-CF$_3$). Copper bromide for the preparation of compound of the formula (V) would also come with waste disposal problems upon industrialization of the manufacturing process.

Compound of the Formula (III) to Compound of the Formula (XVI-Cl)/(XVI-CF$_3$) (Present Invention)

The sequence described in the present invention reduces the sequence length and the associated problems dramatically by the use of different synthetic intermediates and more advantageous reaction conditions. The first transformation of 2,5-dimethoxypyridine (III) to (2,5-dimethoxypyridin-4-yl)boronic acid (IV) remains the same with improved yield, due to improved reaction conditions and work-up procedure. In contrast to the previously described reaction conditions the transformation can now be conducted at −60° C. instead of −78° C., which represents an advantage for the industrialization of the process. Furthermore, for the quality and the yield of the product it is beneficial to prepare the lithium diisopropylamide directly in situ and not use the commercially available solution of lithium diisopropylamide. After completion of the reaction it is quenched with a mixture of acetic acid and water and the remaining organic solvent removed under vacuum with temperatures not exceeding 70° C. (stability of the product).

The obtained (2,5-dimethoxypyridin-4-yl)boronic acid (IV) is directly coupled with the 1-(2-bromo-4-chlorophenyl)-4-chloro-1H-1,2,3-triazole (X-Cl)/1-(2-bromo-4-chlorophenyl)-4-(trifluoromethyl)-1H-1,2,3-triazole (X-CF$_3$) to give the 4-[5-chloro-2-(4-chloro-1H-1,2,3-triazol-1-yl)phenyl]-2,5-dimethoxy-pyridine (XV-Cl)/4-{5-chloro-2-[4-(trifluoromethyl)-1H-1,2,3-triazol-1-yl]phenyl}-2,5-dimethoxypyridine (XV-CF$_3$) without going via another bromination/boronic ester installation step. The cross-coupling reaction is performed under robust and reliable conditions with a Pd-catalyst system with a base in a solvent that allows for an efficient coupling and work-up process that removes remaining palladium and results in a convenient crystallization of the target compound from the work-up mixture in excellent quality. Key to this improved work-up procedure is the switch of the Pd-catalyst system to Pd(Amphos)$_2$Cl$_2$ (A. S. Guram, et al., *Organic Letters*, 2006, 8, 1787), implementation of a dosing strategy and the switch of the reaction solvent from THF to tert-amyl-alcohol.

The reaction works well with various Pd-catalyst systems such as Pd(OAc)$_2$/PPh$_3$, Pd(Amphos)$_2$Cl$_2$ or precatalyst systems. Particularly good results are obtained using Pd(Amphos)$_2$Cl$_2$ as the Pd-catalyst system. The Pd-catalyst system is used in a ratio of 0.5 mol % to 5 mol %, preferably at a ratio of 0.7 mol % to 1.3 mol % and very preferably at a ratio of 1 mol % based on the compound of the formula (X-Cl)/(X-CF$_3$).

As a base various inorganic bases can be used in this process. Particular preference is given to bases such as potassium phosphate, potassium hydrogenphosphate, sodium or potassium carbonate with a particular preference for sodium carbonate. The respective base is used as a solution in water. The base is used in a ratio of from 2 to 4 molar equivalents based on the compound of the formula (X-Cl)/(X-CF$_3$) with preference for a ratio of 2.5 to 3.5 molar equivalents and with particular preference for a ratio of 3 molar equivalents.

(2,5-Dimethoxypyridin-4-yl)boronic acid (IV) is used in a ratio of 1.0 to 1.5 molar ratio. Preferably it is used at a ratio of 1.2 to 1.4 molar equivalents based on the compound of the formula (X-Cl) and very preferably it is used at a ratio of 1.2 molar equivalents based on the compound of the formula (X-C). Preferably it is used at a ratio of 1.05 to 1.15 molar equivalents based on the compound of the formula (X-CF$_3$) and very preferably it is used at a ratio of 1.07 molar equivalents based on the compound of the formula (X-CF$_3$).

As a solvent various high boiling organic solvents such as alcohols or tetrahydrofuran can be used. Preferred alcohols are 2-propanol, 1-propanol, 1-butanol or tert-amyl-alcohol (2-methyl-2-butanol), preferred is tert-amyl-alcohol (2-methyl-2-butanol). Particular preferred is the use of tert-amyl-alcohol (2-methyl-2-butanol) in a ratio of 1:10 (m/v) based on the compound of the formula (X-Cl)/(X-CF$_3$). tert-Amyl-alcohol (2-methyl-2-butanol) proves especially useful as it provides excellent conversion rates, which results in a short reaction time, and allows for the possibility of high reaction temperatures and good phase separations from aqueous phases during work-up.

The reaction temperature is preferably in a range from 55° C. to 100° C. with a particular preference for the temperature range from 63° C. to 67° C. for the compound of the formula (XV-Cl) and from 93° C. to 97° C. for the compound of the formula (XV-CF$_3$).

In order to avoid the formation of side products, namely a second coupling of the compound of the formula (XV-Cl)/(XV-CF$_3$) with another molecule of the compound of the formula (IV) via the chloride in the phenyl ring, a dosing strategy is used.

A slow addition of (2,5-dimethoxypyridin-4-yl)boronic acid (IV) to the active catalytic system (Pd-catalyst system with compound of the formula (X-Cl)/(X-CF$_3$)) is chosen to ensure selectivity for the coupling of (2,5-dimethoxypyridin-4-yl)boronic acid (IV) with the bromide in the compound of the formula (X-Cl)/(X-CF$_3$) over the non-desired second coupling with the primary coupling product which means reaction with the chloride in the phenyl ring of the compound of the formula (XV-Cl)/(XV-CF$_3$). The dosing of a solution of the compound of the formula (IV) and the base in water is done in a time range of 0.5 to 5 hours and preferably between 1 and 4 hours. Particularly advantageous is the addition of the above specified mixture in 2 to 3 hours, preferably 2.5 hours, for the preparation of the compound of the formula (XV-Cl) and in 3 to 4 hours, preferably 4 hours, for the preparation of the compound of the formula (XV-CF$_3$).

The obtained compound of the formula (XV-Cl)/(XV-CF$_3$) is directly used in a demethylation reaction that selectively removes one of the two methyl groups (the methyl group in neighborhood to the nitrogen) to obtain the pyridone which is the compound of the formula (XVI-Cl)/(XVI-CF$_3$).

The demethylation is performed under very advantageous conditions with inexpensive lithium chloride and p-toluenesulfonic acid. The demethylation reaction is performed in polar and high boiling solvents such as alcohols or ethylene glycol. Since a reaction temperature of ≥75° C. is necessary, alcohols with ≥3 carbon atoms are required, for example 2-propanol, 1-propanol, 1-butanol or tert-amyl-alcohol (2-methyl-2-butanol). The preferred temperature range for the demethylation is between 75° C. and 120° C. Of particular preference is the use of 2-propanol at reflux temperature for the reaction. This solvent choice allows for a very convenient work-up procedure. Simple addition of water at reflux temperature and cooling to lower temperatures results in precipitation of the compound of the formula (XVI-Cl)/(XVI-CF$_3$) in excellent quality and yield.

The described synthetic steps represent an important shortcut in the overall synthesis of the comparable synthetic intermediates the compound of the formula (XI-Cl)/(XI-CF$_3$) and the compound of the formula (XVI-Cl)/(XVI-CF$_3$). In both formulae the triazol is coupled with the pyridone core and for completion of the structural entity attachment of the benzamide is required. In other words, both intermediates, the compound of the formula (XI-Cl)/(XI-CF$_3$) and the compound of the formula (XVI-Cl)/(XVI-CF$_3$), are only one more structure forming synthetic step away from the intermediate that contains all the structural elements of the final target compound of the formula (I)/(II). While the synthesis route described in WO 2017/005725 requires 6 steps with an overall yield of 9.3%, the synthesis route of the present invention needs only 3 steps with an overall yield of 47%.

b) Compound of the formula (XI-Cl)/(XI-CF$_3$) to compound of the formula (XIV-Cl)/(XIV-CF$_3$) (described in WO 2017/005725) versus compound of the formula (XVI-Cl)/(XVI-CF$_3$) to compound of the formula (I)/(II) (present invention)

Compound of the Formula (XI-Cl)/(XI-CF$_3$) to Compound of the Formula (XIV-Cl)/(XIV-CF$_3$) (Described in WO 2017/005725)

In WO 2017/005725 the intermediate compound of the formula (XI-Cl)/(XI-CF$_3$) is moved forward in a linear sequence to the racemic version of the target compound of the formula (XVI-Cl)/(XVI-CF$_3$). Therefore the tert.-butyl ester of the compound of the formula (XI-Cl)/(XI-CF$_3$) is converted in an acidic ester hydrolysis into the carboxylic acid of the compound of the formula (XII-Cl)/(XII-CF$_3$) using 4M hydrogen chloride in dioxane. The compound of the formula (XII-Cl)/(XII-CF$_3$) is then coupled with 4-amino-2-fluorobenzamide (XIII) to give the compound of the formula (XIV-Cl)/(XIV-CF$_3$). Deprotection of the tert.- butyl ester adds another non-productive step to the sequence, as no additional bonds of the final compound are formed. One of the largest drawbacks of the entire synthesis is that the initial product of the sequence described in WO 2017/005725, the compound of the formula (XIV-Cl)/(XIV-CF$_3$), is fully racemic and chances to obtain enantiomerically pure material with this sequence are very limited (see literature precedence mentioned above).

Compound of the Formula (XVI-Cl)/(XVI-CF$_3$) to Compound of the Formula (I)/(II) (Present Invention)

In the present invention the entire eastern part of the compound of the formula (I)/(II) which is the compound of the formula (XIX) is prepared separately and coupled to the compound of the formula (XVI-Cl)/(XVI-CF$_3$) in the last step which adds a high level of convergency to the synthetic strategy. In order to obtain high levels of enantiomeric purity the final step needs to proceed as a pure SN$_2$-reaction with full inversion of the stereocenter to form the compound of the formula (I)/(II) from the enantiomerically pure R-stereoisomer 4-{[(2R)-2-bromobutanoyl]amino}-2-fluorobenzamide (XIX).

The preparation of 4-{[(2R)-2-bromobutanoyl]amino}-2-fluorobenzamide (XIX) starts from (2R)-2-aminobutanoic acid (XVII) which is easily converted into (2R)-2-bromobutanoic acid (XVIII) with potassium bromide and sodium nitrite in aqueous sulfuric acid (H. Rapoport, et al., *J. Org. Chem.*, 1986, 51, 1713).

The enantiomerically pure (2R)-2-bromobutanoic acid (XVIII) is then coupled to 4-amino-2-fluorobenzamide (XIII) to yield 4-{[(2R)-2-bromobutanoyl]amino}-2-fluorobenzamide (XIX) which is together with the pyridone, which is the compound of the formula (XVI-Cl)/(XVI-CF$_3$), the direct precursor for the preparation of the compound of the formula (I)/(II). The coupling works in case of the carboxylic acid with carbodiimides, such as EDC or DIC, or with the here applied T$_3$P/pyridine coupling system (J. R. Dunetz, et al., *Org. Lett.*, 2011, 13, 5048) as coupling reagents, or via the carboxylic acid chloride optionally in the presents of a base, in example triethylamine. The procedure developed for the coupling relying on T$_3$P/pyridine as the reagent system proves especially useful and allows for an amide formation without any racemization at the chiral centre of the compound of the formula (XIX) during reaction and work-up. In the process preference is given to using from 1.1 to 2.2 molar equivalents of T$_3$P and 0.5 to 3.5 molar equivalents of pyridine while the reaction is performed in a temperature range between 0° C. and 40° C. Preferred is the use of 1.2 to 1.8 molar equivalents of T$_3$P, particularly preferred is the use of 1.5 molar equivalents of T$_3$P. Preferred is the use of 0.8 to 2.5 molar equivalents of pyridine, particularly preferred is the use of 1.1 molar equivalents of pyridine. The preferred reaction temperature is 15° C. to 30° C., the particularly preferred reaction temperature is 22° C. Due to the solubility properties of the compound of the formula (XIX) tetrahydrofuran is particularly useful as a solvent.

A for the present invention carefully developed work-up procedure based on water addition and seeding allows for crystallization of the compound of the formula (XIX) from the work-up mixture in excellent quality and yield without erosion of the enantioselectivity. Therefore, the avoidance of halide counter ions coming from washing solutions, such as aqueous sodium chloride solution and aqueous ammonium chloride solution, is necessary. The work-up procedure is carried out as follows. In the first step addition of water is done, preferably in a ratio of 1:8 to 1:12 (m/v) based on the compound of the formula (XVIII), most preferably in a ratio of 1:10 (m/v). Then the mixture is seeded with the compound of the formula (XIX) and more water preferably in a ratio of 1:4 to 1:8 (m/v) based on the compound of the formula (XVIII), most preferably in a ratio of 1:6 (m/v), is added. Removal of tetrahydrofuran via distillation under vacuum results in an easy-to-filter suspension that contained the compound of the formula (XIX) in high yield and excellent quality.

Finally, the compound of the formula (XIX) and the compound of the formula (XVI-Cl)/(XVI-CF$_3$) are coupled in a base mediated N-alkylation reaction. The challenge of this transformation is to find reaction conditions that are at the same time optimal with regards to conversion (time and yield), N/O-alkylation selectivity and enantioselectivity. The base needs to have pKa>13 in water and is preferably a non-ionic organic base. Weaker bases result in no or not sufficient conversion, while stronger ionic bases are also inferior in terms of conversion and enantioselectivity and N/O-alkylation selectivity. Best results are obtained with strong non-ionic organic bases such as amidine, guanidine or phosphazene bases. Preferred non-ionic organic bases are 1,8-diazabicyclo[5.4.0]undec-7-ene, N,N,N,N-tetramethylguanidine and 2-tert-butylimino-2-diethylamino-1,3-dimethylperhydro-1,3,2-diazaphosphorine. Particularly preferred is the base N,N,N,N-tetramethylguanidine as it is inexpensive and mediates the reaction with good conversion rates, as well as good enantioselectivity and N/O-alkylation selectivity. Furthermore, N,N,N,N-tetramethylguanidine is water miscible, which allows for an easy removal during aqueous work-up. The base is used in a ratio from 0.8 to 5 molar equivalents based on the compound of the formula (XVI-Cl)/(XVI-CF$_3$), with preference for a ratio of 1.1 to 3 molar equivalents. Particularly preferred is a range of 1.2 to 1.6 molar equivalents based on the compound of the formula (XVI-Cl)/(XVI-CF$_3$).

As solvent many organic solvents pure or in mixtures can be used with one or the other advantage in example in N/O-alkylation selectivity or enantioselectivity or yield or conversion time. Alcohols provide a very good N/O-alkylation selectivity. Preferably good results are obtained with tert-butanol, 1-butanol or 2-propanol. However these solvents are unsatisfying in terms of solubility and conversion. None of the reactions is complete in 50 hours. The reaction time is over 50 hours and in many cases does not go to full completion. On the other hand polar non-protic solvents such as tetrahydrofuran, N,N-dimethylformamide, dioxane or acetone result in complete conversion in less than 3 hours, but suffer from poor selectivity of the preferred N-alkylation over the undesired O-alkylation. As a consequence mixtures of the solvents are used to combine the good conversions observed with the more polar non-protic solvents with the high enantioselectivity and N/O-alkylation selectivity observed in alcohols. While many mixtures of the above mentioned solvents work, preferred is the combination of acetone and 1-butanol or acetone and 2-propanol. Of particular preference is the mixture of acetone and 2-propanol. The mixture is used in a range of 1:2 to 1:9 acetone/2-propanol, with a particular preference for the ratio 1:3 to 1:5 acetone/2-propanol.

The temperature range of the reaction is between 0° C. and 60° C. to obtain reasonable conversions. However at the higher end of this temperature range the enantioselectivities obtained are in general not satisfying. Reactions at the lower end of the described temperature range require longer conversion times that in turn also are detrimental for the enantioselectivities obtained. Therefore a preferred temperature range is identified between 15° C. and 25° C., with a particularly preferred temperature range between 18° C. and 23° C.

In summary, a mixture of a protic (i.e. alcohol) and a polar non-protic solvent at moderate temperatures (from 15° C. to 25° C.) is preferred to obtain a good overall conversion and a good enantioselectivity and N/O-alkylation selectivity. Best results are obtained with 1:4 mixtures of acetone and alcohols at 20° C. reaction temperature. The compound of the formula (I)/(II) is obtained in an amorphous form with high ee-values of 85% ee to 93% ee after filtration and evaporation of the solvents. Furthermore, the preferred N-alkylation over the undesired O-alkylation is obtained in a ratio of N-alkylation to O-alkylation of 9:1 to 10:1.

c) Compound of the formula (XIV-Cl)/(XIV-CF$_3$) to compound of the formula (I)/(II) via chiral separation (described in WO 2017/005725) versus enrichment of the desired enantiomer of the compound of the formula (I)/(II) (present invention)

Compound of the Formula (XIV-Cl)/(XIV-CF$_3$) to Compound of the Formula (I)/(II) Via Chiral Separation (Described in WO 2017/005725)

The preparation of the compound of the formula (I)/(II) described in WO 2017/005725 relies on the separation of the two enantiomers of racemic compound of the formula (XIV-Cl)/(XIV-CF$_3$) via chiral supercritical fluid chromatography (SFC). This represents a very expensive and time-consuming procedure which is not suited to enable production of the compound of the formula (I)/(II) on larger scales. This is particularly true, since throughput times on a standard laboratory SFC are already very low (3-4 g eutomer/day/machine). On top of this, half of the material produced is the undesired enantiomer and cannot be used right away, but needs to be exposed to racemization conditions and to SFC-separation again.

Enrichment of the Desired Enantiomer of the Compound of the Formula (I)/(II) (Present Invention)

In contrast, the procedure described in the present invention shows an easy and scalable way to achieve enrichment of the desired enantiomer in ee-values of >99% ee. The enantiomerically pure compound of the formula (I)/(II) is present in an amorphous solid state form, whereas the racemic material of the compound of the formula (I)/(II) (which is herein the same as the compound of the formula (XIV-Cl)/(XIV-CF$_3$)) is crystalline with much lower solubility in organic solvents. The organic solvent is ethyl acetate, dichloromethane, methanol, 2-propanol, acetone and mixtures thereof, very preferably the solvent is ethyl acetate. Based on this principle of different solubility of the desired enantiomerically pure compound of the formula (I)/(II) and the racemic material of the compound of the formula (I)/(II), the product with ee-values of 85% ee to 93% ee (as mentioned above) is dissolved in a defined amount of ethyl acetate heated to reflux and stirred. Preference is given for a ratio of compound of the formula (I)/(II) to ethyl acetate of 1:1 to 1:10 (m/m), with particular preference for a ratio of compound of the formula (I)/(II) to ethyl acetate of 1:2 to 1:5 (m/m). The less soluble crystalline racemic compound of the formula (I)/(II) forms a suspension, while the desired enantiomerically pure amorphous material of the compound of the formula (I)/(II) is dissolved in the organic solvent. Hot filtration separates the crystalline racemate from the further enantioenriched single enantiomer. Via the racemate the remaining undesired enantiomer is removed from the product and ee-values >99% ee are obtained. This means the enantiomerically pure compound of the formula (I)/(II) (ee-values >99% ee) is obtained by heating the compound of the formula (I)/(II) with ee-values of 85% ee to 93% ee to reflux in an organic solvent, preferred is ethyl acetate, and subsequent filtration. Solvent evaporation from the filtrate gives the enantiomerically pure compound of the formula (I)/(II) (ee-values >99% ee), which is further purified by normal-phase column chromatography to separate from other chemical impurities. Other chemical impurities are side products generated during the reaction.

In an alternative procedure purification of the crude product of the compound of the formula (I)/(II) is achieved via crystallization of the enantiomerically enriched compound of the formula (I)/(II) as a solvate. The respective solvent for the solvate is ethyl acetate, isopropyl acetate, tetrahydrofuran or acetone, preferably acetone is used. As a solvate, crystalline phases of the enantiomerically enriched compound of the formula (I)/(II) and in particular of the enantiomerically enriched compound of the formula (II) can be obtained allowing for an efficient purge of organic side products still present in the crude product of the compound of the formula (I)/(II). The advantage of the solvates is therefore that a purification step can be performed via the crystallisation of solvates.

The crystals formed as solvates, which are especially the compounds of the formula (IIa), (IIb) and (IIc), dissolve better in organic solvents than the racemic crystals of the compound of the formula (II) as such. Therefore, the crystals formed as solvates are dissolved in organic solvent such as ethanol, followed by filtering off the remaining racemic crystals of the compound of the formula (II) which results in a solution containing the compound of the formula (II) with an ee-enrichment. The compound of the formula (II) with ee-values >99% ee is isolated by slowly dosing of the solution into cold water and subsequent filtration. The advantage of the solvates is therefore that a purge of side products for the compound of the formula (II) can be performed via the solvates and this can be combined with the subsequent ee-enrichment via removal of crystalline racemate.

Enantiomerically enriched compound means a compound with preferably ee-values of 85% ee to 93% ee, but the enantiomeric purity can also be below ee-values of 85% ee or above ee-values of 93% ee for this purification step.

Overall the new synthetic route described in the present invention is more efficient, economic and time optimized for the manufacturing of kilogram amounts of the compound of the formula (I)/(II). The longest linear sequence is four synthetic steps and the overall yield of the six steps in total is 20% to 25%. Furthermore, the synthesis of the present invention requires less steps of introducing and removing protection groups which do not directly contribute to the build-up of the compound of the formula (I)/(II).

The present invention also covers a process for preparing 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I) or 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide (II), characterized in that respectively 4-[5-chloro-2-(4-chloro-1H-1,2,3-triazol-1-yl)phenyl]-5-methoxypyridin-2(1H)-one (XVI-Cl) or 4-{5-chloro-2-[4-(trifluoromethyl)-1H-1,2,3-triazol-1-yl]phenyl}-5-methoxypyridin-2(1H)-one (XVI-CF$_3$) is reacted with 4-{[(2R)-2-bromobutanoyl]amino}-2-fluorobenzamide (XIX) in the presence of a base in a solvent and the compound of the formula (I) or (II) is subsequently isolated.

The present invention also covers a process for preparing 4-{[(2R)-2-bromobutanoyl]amino}2-fluorobenzamide (XIX) by reaction of (2R)-2-bromobutanoic acid (XVIII) with 4-amino-2-fluorobenzamide (XIII).

The present invention also covers a process for preparing 4-{5-chloro-2-[4-(trifluoromethyl)-1H-1,2,3-triazol-1-yl]phenyl}-5-methoxypyridin-2(1H)-one (XVI-CF₃) by reaction of 4-{5-chloro-2-[4-(trifluoromethyl)-1H-1,2,3-triazol-1-yl]phenyl}-2,5-dimethoxypyridine (XV-CF₃) with lithium chloride and p-toluenesulfonic acid in a solvent.

The present invention also covers a process for preparing 4-{5-chloro-2-[4-(trifluoromethyl)-1H-1,2,3-triazol-1-yl]phenyl}-2,5-dimethoxypyridine (XV-CF₃) by reaction of (2,5-dimethoxypyridin-4-yl)boronic acid (IV) with 1-(2-bromo-4-chlorophenyl)-4-(trifluoromethyl)-1H-1,2,3-triazole (X-CF₃) in the presence of a Pd-catalyst system with a base in a solvent.

The present invention also covers a process for preparing 4-[5-chloro-2-(4-chloro-1H-1,2,3-triazol-1-yl)phenyl]-5-methoxypyridin-2(1H)-one (XVI-Cl) by reaction of 4-[5-chloro-2-(4-chloro-1H-1,2,3-triazol-1-yl)phenyl]-2,5-dimethoxy-pyridine (XV-Cl) with lithium chloride and p-toluenesulfonic acid in a solvent.

The present invention also covers a process for preparing 4-[5-chloro-2-(4-chloro-1H-1,2,3-triazol-1-yl)phenyl]-2,5-dimethoxy-pyridine (XV-Cl) by reaction of (2,5-dimethoxypyridin-4-yl)boronic acid (IV) with 1-(2-bromo-4-chlorophenyl)-4-chloro-1H-1,2,3-triazole (X-Cl) in the presence of a Pd-catalyst system with a base in a solvent.

The present invention also covers a process for preparing 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I), characterized in that
  i.) in the first step, (2,5-dimethoxypyridin-4-yl)boronic acid (IV) is reacted with 1-(2-bromo-4-chlorophenyl)-4-chloro-1H-1,2,3-triazole (X-Cl) in the presence of a Pd-catalyst system with a base in a solvent to form 4-[5-chloro-2-(4-chloro-1H-1,2,3-triazol-1-yl)phenyl]-2,5-dimethoxy-pyridine (XV-Cl),
  ii.) in the second step, 4-[5-chloro-2-(4-chloro-1H-1,2,3-triazol-1-yl)phenyl]-2,5-dimethoxy-pyridine (XV-Cl) is reacted with lithium chloride and p-toluenesulfonic acid in a solvent to form 4-[5-chloro-2-(4-chloro-1H-1,2,3-triazol-1-yl)phenyl]-5-methoxypyridin-2(1H)-one (XVI-Cl),
  iii.) in the third step, 4-[5-chloro-2-(4-chloro-1H-1,2,3-triazol-1-yl)phenyl]-5-methoxypyridin-2(1H)-one (XVI-Cl) is reacted with 4-{[(2R)-2-bromobutanoyl]amino}-2-fluorobenzamide (XIX) in the presence of a base in a solvent and the compound of the formula (I) is subsequently isolated.

The present invention also covers a process for preparing 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide (II), characterized in that
  i.) in the first step, (2,5-dimethoxypyridin-4-yl)boronic acid (IV) is reacted with 1-(2-bromo-4-chlorophenyl)-4-(trifluoromethyl)-1H-1,2,3-triazole (X-CF₃) in the presence of a Pd-catalyst system with a base in a solvent to form 4-{5-chloro-2-[4-(trifluoromethyl)-1H-1,2,3-triazol-1-yl]phenyl}-2,5-dimethoxypyridine (XV-CF₃),
  ii.) in the second step, 4-{5-chloro-2-[4-(trifluoromethyl)-1H-1,2,3-triazol-1-yl]phenyl}-2,5-dimethoxypyridine (XV-CF₃) is reacted with lithium chloride and p-toluenesulfonic acid in a solvent to form 4-{5-chloro-2-[4-(trifluoromethyl)-1H-1,2,3-triazol-1-yl]phenyl}-5-methoxypyridin-2(1H)-one (XVI-CF₃),
  iii.) in the third step, 4-{5-chloro-2-[4-(trifluoromethyl)-1H-1,2,3-triazol-1-yl]phenyl}-5-methoxypyridin-2(1H)-one (XVI-CF₃) is reacted with 4-{[(2R)-2-bromobutanoyl]amino}-2-fluorobenzamide (XIX) in the presence of a base in a solvent and the compound of the formula (II) is subsequently isolated.

The present invention also covers a process for preparing 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide (II), characterized in that the subsequent isolation is performed via the 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide acetone (IIc).

Synthesis Sequences of the Invention

The compound of the formula (XVII) is converted to the compound of the formula (XVIII).

The compound of the formula (XVIII) is reacted with the compound of the formula (XIII) to give the compound of the formula (XIX).

The compound of the formula (III) is converted to the compound of the formula (IV).

The compound of the formula (IV) is reacted with the compound of the formula (X-Cl) to give the compound of the formula (XV-Cl).

The compound of the formula (IV) is reacted with the compound of the formula (X-CF₃) to give the compound of the formula (XV-CF₃).

The compound of the formula (XV-Cl) is converted to the compound of the formula (XVI-Cl).

The compound of the formula (XV-CF₃) is converted to the compound of the formula (XVI-CF₃).

The compound of the formula (XVI-Cl) is reacted with the compound of the formula (XIX) to give the compound of the formula (I).

The compound of the formula (XVI-CF₃) is reacted with the compound of the formula (XIX) to give the compound of the formula (II).

The present invention also covers 4-[5-chloro-2-(4-chloro-1H-1,2,3-triazol-1-yl)phenyl]-2,5-dimethoxy-pyridine of the formula

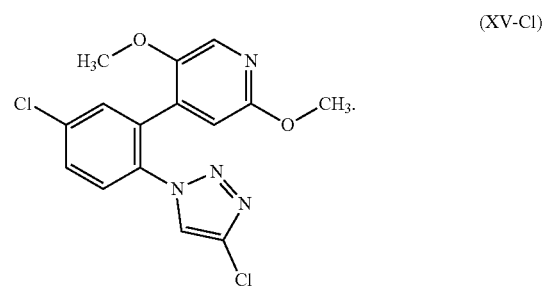 [SMILES: COc1cc(-c2cc(Cl)ccc2-n2cc(Cl)nn2)c(OC)cn1]

(XV-Cl)

The present invention also covers 4-{5-chloro-2-[4-(trifluoromethyl)-1H-1,2,3-triazol-1-yl]phenyl}-2,5-dimethoxy-pyridine of the formula

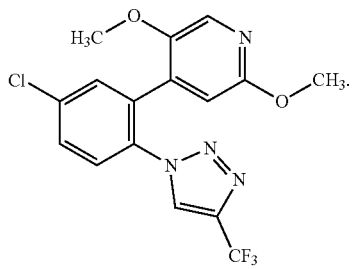

(XV-CF₃)

The present invention also covers 4-[5-chloro-2-(4-chloro-1H-1,2,3-triazol-1-yl)phenyl]-5-methoxypyridin-2(1H)-one of the formula

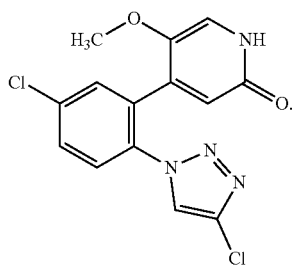

(XVI-Cl)

The present invention also covers 4-{5-chloro-2-[4-(trifluoromethyl)-1H-1,2,3-triazol-1-yl]phenyl}-5-methoxypyridin-2(1H)-one of the formula

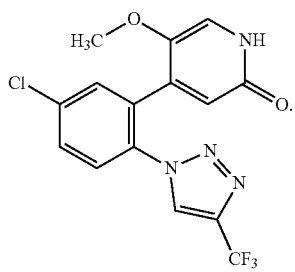

(XVI-CF₃)

The present invention also covers 4-{[(2R)-2-bromobutanoyl]amino}-2-fluorobenzamide of the formula

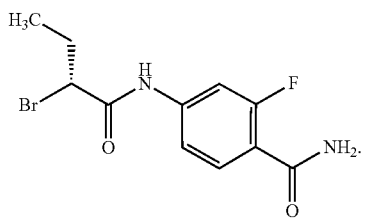

(XIX)

The present invention also covers 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide isopropyl acetate of the formula

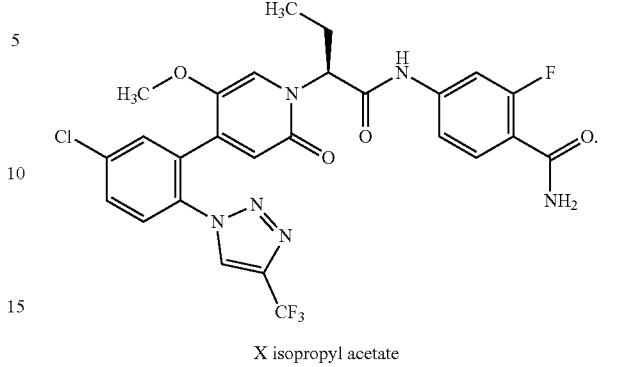

(IIa)

X isopropyl acetate

The present invention also covers 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide tetrahydrofuran of the formula

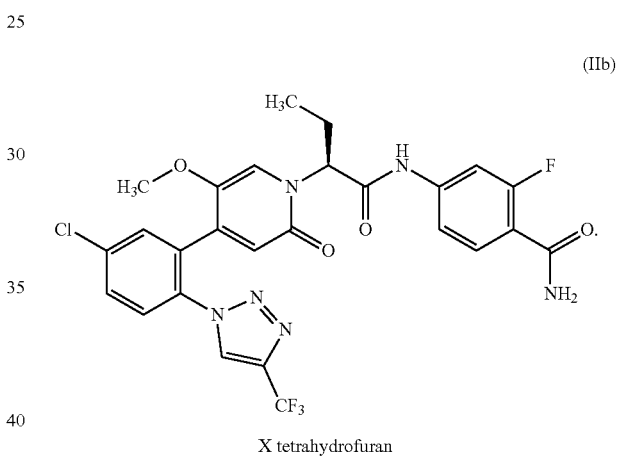

(IIb)

X tetrahydrofuran

The present invention also covers 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide acetone of the formula

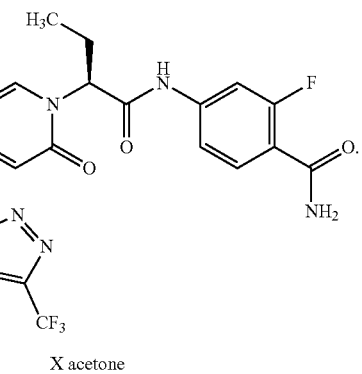

(IIc)

X acetone

EXAMPLES

Abbreviations and Acronyms

Pd(amphos)$_2$Cl$_2$ Bis[(dicyclohexyl)(4-dimethylaminophenyl)phosphine]palladium(II)-chloride
wt % percent by weight
area % percent by area
% of th. percent of theory
corr. corrected
uncorr. uncorrected
min minutes
h hours
mg milligram
g gram
kg kilogram
l litre
ml millilitre
ESI electron spray ionisation
GC gas chromatography
HPLC high pressure (performance) liquid chromatography
SFC supercritical fluid chromatography
Br broad
s singlet
d doublet
t triplet
spt septet
quin quintet
ppm parts per million
m multiplet
Hz hertz
M molar
EDC 1-ethyl-3-(3-dimethylaminopropyl)carbodiimide
DIC N,N'-diisopropylcarbodiimide
T$_3$P propylphosphonic anhydride
THF tetrahydrofuran
(m/m) mass/mass
(m/v) mass/volume
XRPD X-Ray Powder Diffraction
DSC Differential scanning calorimetry The term "the compound of the formula (XVI-Cl)/(XVI-CF$_3$)" does mean that the compound of the formula (XVI-Cl) or the compound of the formula (XVI-CF$_3$) is used according to the synthesis route to the compound of the formula (I) which contains a chlorine substituent or the compound of the formula (II) which contains a trifluoromethyl substituent. The same does also apply for the other terms which means for the compound of the formula (X-Cl)/(X-CF$_3$) and (XI-Cl)/(XI-CF$_3$) and (XII-Cl)/(XII-CF$_3$) and (XIV-Cl)/(XIV-CF$_3$) and (XV-Cl)/(XV-CF$_3$) and (XVI-Cl)/(XVI-CF$_3$) and (I)/(II) as well as if the chemical names of the compounds are used.

If the term "the compound of the formula ( . . . )" is used this term can be replaced by the IUPAC name of the compound of the formula ( . . . ). The IUPAC names of the compounds are mentioned above.

The racemic material of the compound of the formula (I)/(II) is herein the same as the compound of the formula (XIV-Cl)/(XIV-CF$_3$).

In the context of the present invention, the term "enantiomerically pure" is to be understood as meaning that the compound in question with respect to the absolute configuration of the chiral centre is present in an enantiomeric excess of more than 95%, preferably more than 97%. The enantiomeric excess, ee, is calculated here by evaluating the corresponding HPLC chromatogram on a chiral phase using the formula below:

$ee=[E^A \text{ (area \%)} - E^B \text{ (area \%)}] \times 100\% / [E^A \text{ (area \%)} + E^B \text{ (area \%)}]$ ($E^A$: major enantiomer, $E^B$: minor enantiomer)

WORKING EXAMPLES

Synthesis of (2,5-dimethoxypyridin-4-yl)boronic acid (IV)

66.9 g (661.1 mmol) of N,N-diisopropylamine were dissolved in 380 g of THF and cooled to a temperature of −60° C. 395.2 mL (632.4 mmol) of n-butyllithium (1.6 M in hexane) were added within 45 min while keeping the temperature below −50° C. The mixture was stirred at −60° C. for another 15 min. Then 80 g (574.9 mmol) of 2,5-dimethoxypyridine were added within 45 min while keeping the temperature between −50 and −60° C. After completion of the addition the adding funnel was washed with another 10 mL of THF. The reaction mixture was stirred at −60° C. for 2 h, before 118.9 g (632.4 mmol) triisopropyl borate was added within 30 min. Again the adding funnel was washed with 10 mL of THF. The reaction mixture was warmed to 20° C. and stirred for 30 min.

Then a mixture of acetic acid (106 g) and water (602 g) was added within 15 min and the mixture was stirred for another 30 min. Then the organic solvents (650 g) were evaporated in vacuo (300 mbar) at a temperature of maximum 70° C. and the resulting suspension cooled to 20° C. and filtered. The product cake was washed with cold water (three times 100 mL) and dried at 40° C. for about 16 hours under reduced pressure in a drying oven. Yield: 78.6 g (75% of theory).

MS (ESI+): m/z=184.1 [M+H]$^+$;
$^1$H-NMR (400 MHz, DMSO-d$_6$): δ [ppm]=8.15 (br s, 2H), 7.80 (s, 1H), 6.76 (s, 1H), 3.78 (d, 6H).

Synthesis of 4-[5-chloro-2-(4-chloro-1H-1,2,3-triazol-1-yl)phenyl]-2,5-dimethoxy-pyridine (XV-Cl)

5 g (17.1 mmol) of 1-(2-bromo-4-chlorophenyl)-4-chloro-1H-1,2,3-triazole (X-Cl) and 121 mg (0.17 mmol) Pd(amphos)$_2$Cl$_2$ were suspended in 40.3 g of tert-amyl-alcohol. The reaction mixture was heated to 65° C. and a mixture of 5.4 g (51.2 mmol) sodium carbonate and 3.8 g (20.5 mmol) (2,5-dimethoxypyridin-4-yl)boronic acid (IV) in water (35 mL) was added over 1 h. The reaction mixture was stirred at 65° C. for another 5 h until complete consumption of the triazole (X-Cl) was observed. Then 0.8 g (5.1 mmol) N-acetyl-cystein was added and stirred for another 30 min, before another 8 mL of water were added. The mixture was cooled to 8° C. over 40 min and the suspension obtained was filtered. The filter cake was washed with cold ethanol (two times 4 mL) and water (two times 5 mL), before it was dried at 50° C. for about 15 hours under reduced pressure in a drying oven. Yield: 4.46 g (74% of theory).

MS (ESI+): m/z=351.0 [M+H]$^+$;
$^1$H-NMR (400 MHz, DMSO-d$_6$): δ [ppm]=8.56 (s, 1H), 7.68-7.79 (m, 4H), 6.79 (s, 1H), 3.76-3.85 (s, 3H), 3.44 (s, 3H).

Synthesis of 4-{5-chloro-2-[4-(trifluoromethyl)-1H-1,2,3-triazol-1-yl]phenyl}-2,5-dimethoxy-pyridine (XV-CF$_3$)

5 g (15.3 mmol) of 1-(2-bromo-4-chlorophenyl)-4-(trifluoromethyl)-1H-1,2,3-triazole (X-CF$_3$) and 108 mg (0.15 mmol) Pd(amphos)$_2$Cl$_2$ were suspended in 40.3 g of tert-amyl-alcohol. The reaction mixture was heated to 85° C. and a mixture of 4.8 g (45.9 mmol) sodium carbonate and 3.6 g (19.9 mmol) (2,5-dimethoxypyridin-4-yl)boronic acid (IV)

in water (35 mL) was added over 3 h. The reaction mixture was stirred at 85° C. for another 1 h until complete consumption of the triazole (X-CF$_3$). Then 0.8 g (5.1 mmol) N-acetyl-cystein was added and stirred for another 30 min, before 40 mL of tert-amyl alcohol were distilled off and 20 mL of ethanol were added. The mixture was cooled to 2° C. over 120 min and stirred for another 1 h. Then the suspension obtained was filtered. The filter cake was washed with cold ethanol (three times 3 mL) and water (two times 5 mL), before it was dried at 50° C. for about 15 hours under reduced pressure in a drying oven. Yield: 3.62 g (62% of theory).

MS (ESI+): m/z=385.1 [M+H]$^+$;
$^1$H-NMR (400 MHz, DMSO-d$_6$): δ [ppm]=9.14 (s, 1H), 7.82 (s, 2H), 7.73 (s, 2H), 6.84 (s, 1H), 3.81 (s, 3H), 3.38 (s, 3H).

Synthesis of 4-[5-chloro-2-(4-chloro-1H-1,2,3-triazol-1-yl)phenyl]-5-methoxypyridin-2(1H)-one (XVI-Cl)

9.0 g (25.6 mmol) of 4-[5-chloro-2-(4-chloro-1H-1,2,3-triazol-1-yl)phenyl]-2,5-dimethoxypyridine (XV-Cl), 5.4 g (128.1 mmol) of lithium chloride and 1.8 g (46.4 mmol) of p-toluene sulfonic acid were dissolved in 60 ml of 2-propanol and stirred at reflux temperature for about 16 h until complete consumption of the starting material. Then 120 mL of water were added in 60 min and the mixture was cooled to 10° C. in another 60 min. The suspension was filtered and the filter cake was washed with water (three times 20 mL). Then it was dried at 50° C. for about 15 hours under reduced pressure in a drying oven. Yield: 7.46 g (86% of theory).

MS (ESI+): m/z=337.0 [M+H]$^+$;
$^1$H-NMR (500 MHz, DMSO-d$_6$): δ [ppm]=11.24 (br s, 1H), 8.62 (s, 1H), 7.66-7.78 (m, 3H), 6.99 (s, 1H), 6.36 (s, 1H), 3.29 (s, 3H).

Synthesis of 4-{5-chloro-2-[4-(trifluoromethyl)-1H-1,2,3-triazol-1-yl]phenyl}-5-methoxy-pyridin-2(1H)-one (XVI-CF$_3$)

7.0 g (18.2 mmol) of 4-{5-chloro-2-[4-(trifluoromethyl)-1H-1,2,3-triazol-1-yl]phenyl}-2,5-dimethoxypyridine (XV-CF$_3$), 3.9 g (91.0 mmol) of lithium chloride and 6.3 g (32.9 mmol) of p-toluene sulfonic acid were dissolved in 60 ml of 2-propanol and stirred at reflux temperature for about 16 h until complete consumption of the starting material. Then 120 mL of water were added in 60 min and the mixture was cooled to 10° C. in another 60 min. The suspension was filtered and the filter cake washed with water (three times 20 mL). Then it was dried at 50° C. for about 15 hours under reduced pressure in a drying oven. Yield: 6.58 g (97% of theory).

MS (ESI+): m/z=371.0 [M+H]$^+$;
$^1$H-NMR (400 MHz, DMSO-d$_6$): δ [ppm]=11.21 (br s, 1H), 9.18 (s, 1H), 7.81 (s, 2H), 7.72 (s, 1H), 6.95 (s, 1H), 6.41 (s, 1H), 3.23 (s, 3H).

Synthesis of (2R)-2-bromobutanoic acid (XVIII)

In a stirred vessel, 150 g (1454.6 mmol) of (2R)-2-aminobutanoic acid (XVII) and 605.8 g (5091.1 mmol) of potassium bromide were dissolved in 809 g of 2.5 M aqueous sulphuric acid. The mixture was cooled to –10° C. and an aqueous solution of 150.4 g (2181.9 mmol) of sodium nitrite in 150 mL water was added in 30 min. Then the reaction mixture was stirred at 0° C. for 18 h.

After warming the reaction temperature to 20° C. the reaction mixture was extracted with ethyl acetate (three times 500 mL) and the organic layer concentrated in vacuo to obtain the title compound. Yield: 193.9 g (80% of theory).

MS (ESI+): m/z=166.0 [M+H]$^+$;
$^1$H-NMR (500 MHz, DMSO-d$_6$): δ [ppm]=4.28 (dd, 1H), 1.98-2.07 (m, 1H), 1.83-1.94 (m, 1H), 0.97 (t, 3H).

Synthesis of 4-{[(2R)-2-bromobutanoyl]amino}-2-fluorobenzamide (XIX)

5.0 g (32.4 mmol) of 4-amino-2-fluorobenzamid (XIII) was suspended in THF (50 mL) and cooled to 0° C. Then 5.9 g (35.6 mmol) of (2R)-2-bromobutanoic acid (XVIII) and 2.8 g (35.6 mmol) pyridine were added, before 31.0 g (48.6 mmol) of a T$_3$P solution 50% in ethyl acetate was added in 20 min. The mixture was stirred for 10 min and then allowed to warm to 22° C. The mixture was stirred for another 3 h until complete consumption of the starting materials. Then 60 g of water were added in 45 min and seeding crystals were added. The dosing was stopped for 30 min and then another 40 g of water were added in 15 min. The mixture was distilled to remove the solvent until an internal temperature of 40° C. was reached at 300 mbar vacuum. Then it was cooled to room temperature and filtered. The filter cake was washed with cold water (10 mL) and dried at 50° C. for about 16 hours under reduced pressure in a drying oven. Yield: 8.4 g (85% of theory).

MS (ESI+): m/z=303.0 [M+H]$^+$;
$^1$H-NMR (400 MHz, DMSO-d$_6$): δ [ppm]=10.70 (s, 1H), 7.70 (t, 1H), 7.62-7.67 (m, 1H), 7.55 (s, 1H), 7.52 (br s, 1H), 7.35 (dd, 1H), 4.46 (t, 1H), 2.10 (spt, 1H), 1.95 (dquin, 1H), 0.96 (t, 3H).

Synthesis of 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (I)

10.0 g (30 mmol) of 4-[5-chloro-2-(4-chloro-2,3-dihydro-1H-1,2,3-triazol-1-yl)phenyl]-5-methoxypyridin-2(1H)-one (XVI-Cl) were dissolved in 2-propanol (85 mL) and acetone (21 mL) at 22° C. and 10.3 g (90 mmol) N,N,N,N-tetramethylguanidine was added. After stirring for 15 min at 22° C. 9.89 g (33 mmol) 4-{[(2R)-2-bromobutanoyl]amino}-2-fluorobenzamide (XIX) was added and the mixture stirred for 16 h. Then the reaction mixture was filtered and ethyl acetate (125 mL) was added. The organic layer was washed with a saturated aqueous solution of ammonium chloride (125 mL) and saturated aqueous solution of sodium chloride (125 mL). Then the organic layer was concentrated in vacuo. The residue was dissolved in ethyl acetate (140 mL), stirred for 30 min and filtered. The filtrate was concentrated in vacuo and purified via column chromatography (silica gel, hexane/acetone gradient). Yield: 12.5 (75% of theory).

MS (ESI+): m/z=558.1 [M]$^+$;
$^1$H-NMR (400 MHz, DMSO-d$_6$): δ [ppm]=10.78 (s, 1H), 8.62 (s, 1H), 7.62-7.81 (m, 5H), 7.53 (br d, 2H), 7.39 (dd, 1H), 7.18 (s, 1H), 6.48 (s, 1H), 5.54 (dd, 1H), 3.32 (s, 3H), 2.02-2.19 (m, 2H), 0.82 (t, 3H).

Synthesis of 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II)

10.0 g (27 mmol) of 4-{5-chloro-2-[4-(trifluoromethyl)-1H-1,2,3-triazol-1-yl]phenyl}-5-methoxy-pyridin-2(1H)- one (XVI-CF$_3$) were dissolved in 2-propanol (85 mL) and acetone (21 mL) at 22° C. and 9.2 g (81 mmol) N,N,N,N-tetramethylguanidine was added. After stirring for 15 min at 22° C. 9.0 g (30 mmol) 4-{[(2R)-2-bromobutanoyl]amino}-2-fluorobenzamide (XIX) was added and the mixture stirred for 16 h. Then the reaction mixture was filtered and ethyl acetate (125 mL) was added. The organic layer was washed with a saturated aqueous solution of ammonium chloride (125 mL) and a saturated aqueous solution of sodium chloride. The organic layer was concentrated in vacuo. The residue was dissolved in ethyl acetate (140 mL), stirred for 30 min and filtered. The filtrate was concentrated in vacuo and purified via column chromatography (silica gel, hexane/acetone gradient). Yield: 11.1 g (70% of theory).

MS (ESI+): m/z=593.1 [M]$^+$;

$^1$H-NMR (400 MHz, DMSO-d$_6$): δ [ppm]=10.77 (br s, 1H), 9.13 (s, 1H), 7.58-7.95 (m, 5H), 7.53 (br d, 2H), 7.37 (dd, 1H), 7.14 (s, 1H), 6.54 (s, 1H), 5.53 (br dd, 1H), 3.26 (s, 3H), 2.02-2.22 (m, 2H), 0.79 (t, 3H).

Alternative Method:

25.0 g (67 mmol) of 4-{5-chloro-2-[4-(trifluoromethyl)-1H-1,2,3-triazol-1-yl]phenyl}-5-methoxy-pyridin-2(1H)-one (XVI-CF$_3$) were dissolved in 2-propanol (125 mL) and acetone (31.4 mL) at 22° C. and 11.6 g (101 mmol) N,N,N,N-tetramethylguanidine was added. After stirring for 15 min at 22° C. 22.5 g (74 mmol) 4-{[(2R)-2-bromobutanoyl]amino}-2-fluorobenzamide (XIX) was added and the mixture stirred for 16 h. Then the reaction mixture was slowly added on cold (0° C.) water (661 mL). The crude product precipitated and was filtered. The crude product was then suspended in acetone (125 mL) and stirred for 30 min. Then water (98.5 g) was added in 4 h, the mixture was seeded and stirred for another 18 h. The resulting acetone solvate was filtered, dried and redissolved in ethanol (108 mL) at 22° C. The mixture was stirred for 30 min, filtered and the filtrate slowly dosed into cold water (5° C., 427 g). The resulting suspension was filtered and the filter cake washed and dried at 60° C. for 16 h under reduced pressure in a drying oven. Yield: 24.4 g (61% of theory).

Isolation of 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide isopropyl acetate (IIa)

46.9 mg of amorphous 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) solid was weighed into a glass vial and 100 μL of isopropyl acetate was added. The vial was closed and the contents were stirred with a magnetic bar at 25° C. During ca. 1 week of stirring formation of crystalline particles occurred. The resulting suspension was dried on air overnight and the resulting solid used for further experiments.

Subsequently, 198.6 mg of amorphous 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) solid was weighed into a glass vial and 600 μL of isopropyl acetate was added. The vial was closed and the contents were stirred with a magnetic bar at 25° C. for 30 minutes. To the resulting solution a small amount (ca. 5 mg) of the previously isolated solid (as described in the paragraph above) was added as seeds. The contents were further stirred at 25° C. and complete crystallization vas observed within a minute. The resulting suspension was dried on a clay square overnight. FIG. 1 shows the XRPD of the resulting solid of the compound of the formula (IIa), FIG. 4 its DSC and FIG. 7 its microscopic image.

Isolation of 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide tetrahydrofuran (IIb)

53.9 mg of amorphous 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) solid was weighed into a glass vial and 50 μL of THF was added. The vial was closed and the contents were stirred with a magnetic bar at 25° C. During ca. 1 week of stirring formation of crystalline particles occurred. The resulting suspension was dried on air overnight and the resulting solid used for further experiments.

Subsequently, 198.5 mg of amorphous 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) solid was weighed into a glass vial and 600 μL of THF was added. The vial was closed and the contents were stirred with a magnetic bar at 25° C. for 30 minutes. To the resulting solution a small amount (ca. 5 mg) of the previously isolated solid (as described in the paragraph above) was added as seeds. The contents were further stirred at 25° C. and complete crystallization vas observed within 30 minutes. The resulting suspension was dried on a clay square overnight. FIG. 2 shows the XRPD of the resulting solid of the compound of the formula (IIb), FIG. 5 its DSC and FIG. 8 its microscopic image.

Isolation of 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide acetone (IIc)

50.5 mg of amorphous 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) solid was weighed into a glass vial and 50 μL of acetone was added. The vial was closed and the contents were stirred with a magnetic bar at 25° C. During ca. 1 week of stirring formation of crystalline particles occurred. The resulting suspension was dried on air overnight and the resulting solid used for further experiments.

Subsequently, 203.9 mg of amorphous 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}amino)-2-fluorobenzamide (II) solid was weighed into a glass vial and 600 μL of acetone was added. The vial was closed and the contents were stirred with a magnetic bar at 25° C. for 30 minutes. To the resulting solution a small amount (ca. 5 mg) of the previously isolated solid (as described in the paragraph above) was added as seeds. The contents were further stirred at 25° C. and complete crystallization vas observed within a minute. The resulting suspension was dried on a clay square overnight. FIG. 3 shows the XRPD of the resulting solid of the compound of the formula (IIc), FIG. 6 its DSC and FIG. 9 its microscopic image.

X-Ray Diffractometry

The X-Ray Powder Diffraction (XRPD) data was recorded on a Bruker D2 PHASER diffractometer with a LynxEye detector using Cu Kα$_{1,2}$ radiation (1.5418 Å). All samples were measured at ambient temperature. The data were collected in the Bragg-Brentano (θ/2θ) horizontal geometry between 3.00149 and 40.0046° (2θ) in 0.0264119° steps at 0.5 s step$^{-1}$. The X-ray tube was operated at 30 kV and 10 mA.

Differential Scanning Calorimetry (DSC)

Differential scanning calorimetry (DSC) was performed with a Mettler Toledo DSC 2, calibrated with an indium standard. The calorimeter cell was purged with nitrogen, at a rate of 100 ml min⁻¹. About 5-10 mg of each sample as measured in an Al crucible. The temperature program was set in the range 25-260° C. (for isopropyl acetate and tetrahydrofuran solvates) or in the range 25-250° C. (for acetone solvate), at a heating rate of 5° C. min-t. The data was processed using the Mettler Toledo Star System.

X-Ray Powder Diffraction (XRPD) Data of the Compounds of the Formula (IIa), (IIb) and (IIc).

| Reflections (2Θ maximum, °) | | |
|---|---|---|
| compound of the formula (IIa) (Isopropyl acetate solvate) | compound of the formula (IIb) (tetrahydrofuran solvate) | compound of the formula (IIc) (acetone solvate) |
| 7.6 | 7.6 | 7.7 |
| 8.0 | 8.0 | 8.1 |
| 10.3 | 10.3 | 8.9 |
| 11.9 | 11.2 | 10.5 |
| 12.4 | 13.1 | 11.1 |
| 13.4 | 13.7 | 11.9, |
| 13.7 | 14.5 | 13.5 |
| 15.6 | 16.0 | 13.8 |
| 16.1 | 16.4 | 15.0 |
| 16.8 | 16.9 | 15.6 |
| 17.3 | 17.3 | 16.3 |
| 18.0 | 18.1 | 16.7 |
| 18.8 | 19.4 | 17.2 |
| 20.1 | 20.0 | 17.6 |
| 21.2 | 21.1 | 18.0 |
| 22.1 | 22.3 | 19.0 |
| 23.2 | 23.0 | 20.1 |
| 24.2 | 24.0 | 21.4 |
| 24.7 | 26.0 | 22.2 |
| 26.0 | 26.9 | 23.3 |
| 26.9 | 27.5 | 23.8 |
| 27.6 | 28.8 | 24.6 |
| 28.4 | 30.2. | 25.0 |
| 29.5 | | 25.4 |
| 30.1 | | 25.8 |
| | | 29.4 |

The invention claimed is:

1. A process for preparing 4-{[(2S)-2-{4-[5-chloro-2-(4-chloro-1H-1,2,3-triazol-1-yl)phenyl]-5-methoxy-2-oxopyridin-1(2H)-yl}butanoyl]amino}-2-fluorobenzamide (formula I) or 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide (formula II), comprising:
reacting 4-[5-chloro-2-(4-chloro-1H-1,2,3-triazol-1-yl)phenyl]-5-methoxypyridin-2(1H)-one (XVI-Cl) or 4-{5-chloro-2-[4-(trifluoromethyl)-1H-1,2,3-triazol-1-yl]phenyl}-5-methoxypyridin-2(1H)-one (XVI-CF₃) with 4-{[(2R)-2-bromobutanoyl]amino}-2-fluorobenzamide (XIX) in the presence of a base in a solvent and the compound of formula (I) or (II) is subsequently isolated.

2. The process according to claim 1, wherein the process is carried out using N,N,N,N-tetramethylguanidine as base.

3. The process according to claim 1, wherein the process is carried out using a mixture of a protic and a polar non-protic solvent.

4. The process according to claim 1, wherein the process is carried out at a temperature of from 15 to 25° C.

5. The process according to claim 1, wherein the compound of formula (I) or (II) is subsequently isolated in enantiomerically pure form by heating the compound of formula (I) or (II) with ee-values of 85% ee to 93% ee to reflux in an organic solvent and subsequent filtration following evaporation of the organic solvent.

6. The process according to claim 1, wherein 4-{[(2R)-2-bromobutanoyl]amino}-2-fluorobenzamide (XIX) is obtained by reaction of (2R)-2-bromobutanoic acid (XVIII) with 4-amino-2-fluorobenzamide (XIII).

7. The process according to claim 1, wherein 4-{5-chloro-2-[4-(trifluoromethyl)-1H-1,2,3-triazol-1-yl]phenyl}-5-methoxypyridin-2(1H)-one (XVI-CF₃) is obtained, said process comprising reacting 4-{5-chloro-2-[4-(trifluoromethyl)-1H-1,2,3-triazol-1-yl]phenyl}-2,5-dimethoxypyridine (XV-CF₃) with lithium chloride and p-toluenesulfonic acid in a solvent.

8. The process according to claim 7, wherein 4-{5-chloro-2-[4-(trifluoromethyl)-1H-1,2,3-triazol-1-yl]phenyl}-2,5-dimethoxypyridine (XV-CF₃) is obtained, said process comprising reacting (2,5-dimethoxypyridin-4-yl)boronic acid (IV) with 1-(2-bromo-4-chlorophenyl)-4-(trifluoromethyl)-1H-1,2,3-triazole (X-CF₃) in the presence of a Pd-catalyst system with a base in a solvent.

9. The process according to claim 8, wherein the process is carried out using Pd(Amphos)₂Cl₂ as the Pd-catalyst system.

10. The process according to claim 7, wherein the process is carried out using an alcohol as solvent.

11. 4-{5-Chloro-2-[4-(trifluoromethyl)-1H-1,2,3-triazol-1-yl]phenyl}-2,5-dimethoxy-pyridine having the formula

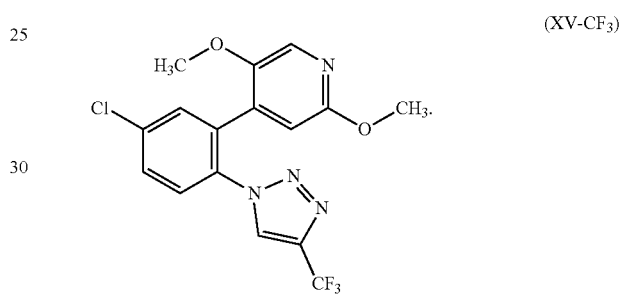

(XV-CF₃)

12. 4-{5-Chloro-2-[4-(trifluoromethyl)-1H-1,2,3-triazol-1-yl]phenyl}-5-methoxy-pyridin-2(1H)-one having the formula

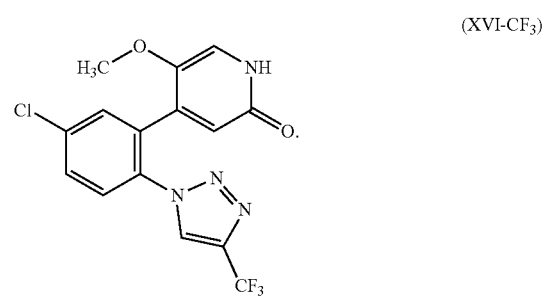 [SMILES: COc1c[nH]c(=O)cc1-c1cc(Cl)ccc1-n1cc(C(F)(F)F)nn1]

(XVI-CF₃)

13. 4-[5-Chloro-2-(4-chloro-1H-1,2,3-triazol-1-yl)phenyl]-2,5-dimethoxy-pyridine having the formula

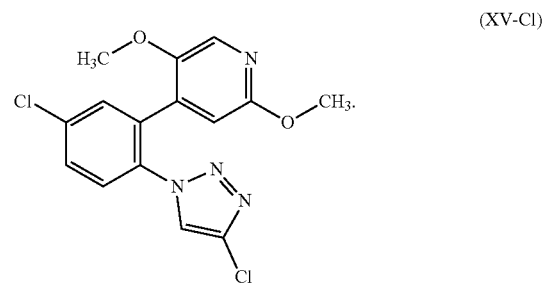 [SMILES: COc1cc(-c2cc(Cl)ccc2-n2cc(Cl)nn2)c(OC)cn1]

(XV-Cl)

14. 4-[5-Chloro-2-(4-chloro-1H-1,2,3-triazol-1-yl)phenyl]-5-methoxypyridin-2(1H)-one having the formula

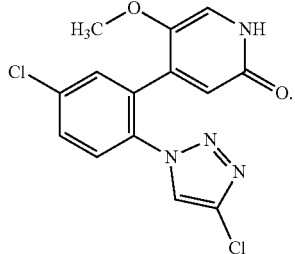

(XVI-Cl)

15. 4-{[(2R)-2-Bromobutanoyl]amino}-2-fluorobenzamide having the formula

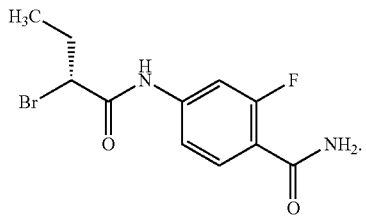

(XIX)

16. 4-({(2S)-2-[4-{-Chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide acetone having the formula

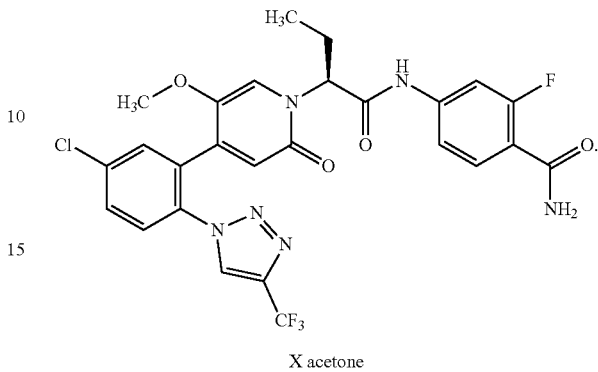

(IIc)

X acetone

17. A process for preparing 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide (II), wherein 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide acetone (IIc) is isolated and converted to 4-({(2S)-2-[4-{5-chloro-2-[4-(trifluoromethyl)-1H-1,2,3-triazol-1-yl]phenyl}-5-methoxy-2-oxopyridin-1(2H)-yl]butanoyl}-amino)-2-fluorobenzamide (II).

* * * * *